US009622974B2

(12) United States Patent
Johnston et al.

(10) Patent No.: US 9,622,974 B2
(45) Date of Patent: Apr. 18, 2017

(54) FORMATION OF STABLE SUBMICRON PEPTIDE OR PROTEIN PARTICLES BY THIN FILM FREEZING

(71) Applicant: Board of Regents, The University of Texas System, Austin, TX (US)

(72) Inventors: Keith P. Johnston, Austin, TX (US); Joshua Engstrom, Spotswood, NJ (US); Robert O. Williams, III, Austin, TX (US)

(73) Assignee: BOARD OF REGENTS, THE UNIVERSITY OF TEXAS, Austin, TX (US)

( * ) Notice: Subject to any disclaimer, the term of this patent is extended or adjusted under 35 U.S.C. 154(b) by 0 days.

(21) Appl. No.: 14/603,211

(22) Filed: Jan. 22, 2015

(65) Prior Publication Data

US 2015/0209289 A1    Jul. 30, 2015

Related U.S. Application Data

(62) Division of application No. 12/665,386, filed as application No. PCT/US2008/067766 on Jun. 20, 2008, now Pat. No. 8,968,786.

(60) Provisional application No. 60/945,737, filed on Jun. 22, 2007.

(51) Int. Cl.
*A61K 9/16* (2006.01)
*B01D 9/00* (2006.01)

(52) U.S. Cl.
CPC .......... *A61K 9/1682* (2013.01); *A61K 9/1658* (2013.01); *B01D 9/005* (2013.01); *Y10T 428/2982* (2015.01)

(58) Field of Classification Search
None
See application file for complete search history.

(56) References Cited

U.S. PATENT DOCUMENTS

| 3,869,549 A | 3/1975 | Geller |
| 4,310,516 A | 1/1982 | Chang et al. |
| 4,588,614 A | 5/1986 | Lauchenauer |
| 4,594,108 A | 6/1986 | Greminger, Jr. et al. |
| 4,848,094 A | 7/1989 | Davis |
| 4,861,760 A | 8/1989 | Mazuel et al. |
| 4,911,920 A | 3/1990 | Jani et al. |
| 5,212,162 A | 5/1993 | Missel et al. |
| 5,300,302 A | 4/1994 | Tachon et al. |
| 5,352,662 A | 10/1994 | Brooks et al. |
| 5,403,841 A | 4/1995 | Lang et al. |
| 5,411,951 A | 5/1995 | Mitchell |
| 5,512,293 A | 4/1996 | Landrau et al. |
| 5,540,912 A | 7/1996 | Roorda et al. |
| 5,571,525 A | 11/1996 | Roorda et al. |
| 5,582,981 A | 12/1996 | Toole et al. |
| 5,595,877 A | 1/1997 | Gold et al. |
| 5,614,221 A | 3/1997 | Fjellstrom |
| 5,635,213 A | 6/1997 | Nystrom et al. |
| 5,637,459 A | 6/1997 | Burke et al. |
| 6,267,958 B1 | 7/2001 | Andya et al. |
| 7,258,869 B1 | 8/2007 | Berry et al. |
| 7,374,782 B2 | 5/2008 | Brown |
| 7,651,770 B2 | 1/2010 | Berkland et al. |
| 7,998,477 B2 | 8/2011 | Yakovlevsky et al. |
| 8,779,094 B2 | 7/2014 | Johnston et al. |
| 8,968,786 B2 * | 3/2015 | Johnston .................. 424/489 |
| 2004/0022861 A1 * | 2/2004 | Williams, III ....... A61K 9/1617 424/489 |
| 2004/0151779 A1 | 8/2004 | Maskiewicz et al. |
| 2004/0197324 A1 | 10/2004 | Liu et al. |
| 2005/0048002 A1 | 3/2005 | Rabinow et al. |
| 2005/0053666 A1 | 3/2005 | Tzannis et al. |
| 2006/0024379 A1 | 2/2006 | Brown et al. |
| 2006/0159756 A1 | 7/2006 | Sjoblom |
| 2006/0193918 A1 | 8/2006 | Rohloff et al. |
| 2007/0015689 A1 | 1/2007 | Rohloff et al. |
| 2007/0154559 A1 | 7/2007 | Pai et al. |

(Continued)

FOREIGN PATENT DOCUMENTS

| CN | 101081882 A | 12/2007 |
| EP | 0225081 A1 | 6/1987 |

(Continued)

OTHER PUBLICATIONS

Bagaria, J.P., "Protein-nanoparticle constructs for intracelluar delivery", Master Thesis in NTNU Norwegian University of Science Technology, Feb. 18, 2011, 108 pages.
Brown, L. R., "Commercial challenges of protein drug delivery." *Expert Opinion on Drug Delivery* 2005, 2(1):29-42.
Chen, G. et al., "Injectable nonaqueous suspension of highly concentrated proteins for non-IV administration.", AAPS Annual Meeting and Exposition, Nashville, TN, 2005; The AAPS Journal: Nashville, TN, 2005, 1 page. (Abstract).
Escaig, J., "New instruments which facilitate rapid freezing at 83 K and 6 K." Journal of Microscopy. (Oxford, United Kingdom) 126:221-230 (1982).
Extended European Search Report dated Jan. 4, 2013 for European Patent Application No. 0877165.7, 8 pages.

(Continued)

*Primary Examiner* — Anand Desai
(74) *Attorney, Agent, or Firm* — Anson M. Nomura; Mintz, Levin, Cohn, Ferris, Glovsky and Popeo, P.C.

(57) ABSTRACT

The present invention includes compositions and methods for preparing micron-sized or submicron-sized particles by dissolving a water soluble effective ingredient in one or more solvents; spraying or dripping droplets solvent such that the effective ingredient is exposed to a vapor-liquid interface of less than 50, 100, 150, 200, 250, 200, 400 or 500 $cm^{-1}$ area/volume to, e.g., increase protein stability; and contacting the droplet with a freezing surface that has a temperature differential of at least 30° C. between the droplet and the surface, wherein the surface freezes the droplet into a thin film with a thickness of less than 500 micrometers and a surface area to volume between 25 to 500 $cm^{-1}$.

12 Claims, 9 Drawing Sheets

(56) References Cited

U.S. PATENT DOCUMENTS

| | | |
|---|---|---|
| 2007/0207210 A1 | 9/2007 | Brown et al. |
| 2008/0102128 A1 | 5/2008 | Constancis |
| 2009/0104271 A1 | 4/2009 | O'Hagan et al. |
| 2009/0191277 A1 | 7/2009 | Aimi |
| 2009/0274765 A1 | 11/2009 | Beduneau et al. |
| 2009/0304599 A1 | 12/2009 | Aimi et al. |
| 2010/0009007 A1 | 1/2010 | Darvari et al. |
| 2010/0047903 A1 | 2/2010 | Piran et al. |
| 2010/0158899 A1 | 6/2010 | Andya et al. |
| 2010/0226928 A1 | 9/2010 | Dani |
| 2010/0247506 A1 | 9/2010 | Johnston et al. |
| 2012/0230913 A1 | 9/2012 | Johnston et al. |
| 2014/0378370 A1 | 12/2014 | Johnston et al. |
| 2016/0058863 A1 | 3/2016 | Johnston et al. |

FOREIGN PATENT DOCUMENTS

| | | |
|---|---|---|
| EP | 0379147 A2 | 7/1990 |
| EP | 1219298 A1 | 7/2002 |
| JP | 08-99897 A | 4/1996 |
| JP | 2007-517023 A | 6/2007 |
| WO | WO-95/34285 A1 | 12/1995 |
| WO | WO-96/05309 A2 | 2/1996 |
| WO | WO-96/05309 A3 | 2/1996 |
| WO | WO-96/40049 A1 | 12/1996 |
| WO | WO-98/00152 A1 | 1/1998 |
| WO | WO-98/00157 A1 | 1/1998 |
| WO | WO-98/00158 A1 | 1/1998 |
| WO | WO-98/16250 A1 | 4/1998 |
| WO | WO-00/45790 A2 | 8/2000 |
| WO | WO-01/89481 A1 | 11/2001 |
| WO | WO-02/060411 A2 | 8/2002 |
| WO | WO-02/067991 A1 | 9/2002 |
| WO | WO-03/009817 A2 | 2/2003 |
| WO | WO-03/009817 A3 | 2/2003 |
| WO | WO-03/009817 A9 | 2/2003 |
| WO | WO-03/032951 A1 | 4/2003 |
| WO | WO-2004/064808 A1 | 8/2004 |
| WO | WO-2004/091658 A1 | 10/2004 |
| WO | WO-2004/112747 A2 | 12/2004 |
| WO | WO-2005/035088 A3 | 4/2005 |
| WO | WO-2005/061004 A1 | 7/2005 |
| WO | WO-2005/061088 A1 | 7/2005 |
| WO | WO-2006/071693 A2 | 6/2006 |
| WO | WO-2009/002874 A1 | 12/2008 |
| WO | WO-2009/137112 A1 | 11/2009 |
| WO | WO-2010/009146 A1 | 1/2010 |
| WO | WO-2010/056657 A2 | 5/2010 |
| WO | WO-2010/139442 A1 | 12/2010 |
| WO | WO-2012/122544 A2 | 9/2012 |
| WO | WO-2012/122544 A3 | 9/2012 |

OTHER PUBLICATIONS

Extended European Search Report dated Nov. 25, 2013 for European Patent Application No. 09826617.4, 10 pages.
Extended European Search Report dated Aug. 20, 2014 for European Patent Application No. 12755064.8, 8 pages.
Gilkey, J.C. et al., "Advances in ultrarapid freezing for the preservation of cellular ultrastructure." Journal of Electron Microscopy Technique 3:177-210 (1986).
"High Concetration Monoclonal Antibody Suspensions for Subcutaneous Injection" presented by Larry Brown et al. Baxter Healthcare Corporation Mar. 2007, 1 page. (Abstract).
"Highly Concentrated Dispersions of Stable Submicron Therapeutic Protein Particles for Subcutaneous Injection." presented by Keith P. Johnston et al. Department of Chemical Engineering, University of Texas—Austin, 2011, 1 page. (Abstract).
Holt et al.: "Role of calcium phosphate nanoclusters in the control of calcification", FEBS Journal, vol. 276, No. 8, Apr. 1, 2009, pp. 2308-2323.
International Preliminary Report on Patentability and Written Opinion dated Dec. 22, 2009 for International Application No. PCT/US2008/067766, 7 pages.
International Preliminary Report on Patentability and Written Opinion dated May 17, 2011 for International Application No. PCT/US2009/063852, 4 pages.
International Preliminary Report on Patentability and Written Opinion dated Sep. 10, 2013 for International Application No. PCT/US2012/028640, 8 pages.
International Search Report dated Sep. 5, 2008 for International Application No. PCT/US2008/067766, 1 page.
International Search Report dated Jul. 27, 2010 for International Application No. PCT/US2009/063852, 3 pages.
International Search Report dated Sep. 10, 2012 for International Application No. PCT/US2012/028640, 5 pages.
Johnston, K.P. et al., "Concentrated dispersions of equilibrium protein nanoclusters that reversibly dissociate into active monomers", ACS Nano, 2013 6(2):1357-1369.
Kanai, S. et al., "Reversible Self-Association of a Concentrated Monoclonal Antibody Solution Mediated by Fab-Fab Interaction That Impacts Solution Viscosity.", Journal of Pharmaceutical Sciences 2008, 97(10):4219-4227.
Maa et al., "Protein Inhalation Powders: Spray Drying vs Spray Freeze Drying", Pharmaceutical Research, 1999, 16(2):249-254.
Maa, Y.F. et al., "Spray freeze-drying of biopharmaceuticals: applications and stability considerations." in: H. R. Costantino and M. J. Pikal (Eds), Biotechnology: Pharmaceutical Aspects. 2. Lyophilization of Biopharmaceuticals, vol. 2 (H. R. Costantino and M. J. Pikal, eds), American Association of Pharmaceutical Scientists, Arlington, 2004, pp. 519-561.
Martins, S. et al., "Lipid-based colloidal carriers for peptide and protein delivery-liposomes versus lipid nanoparticles", International Journal of Nanomedicine 2007, 2(4):595-607.
Miller, M. A., "Highly Concentrated, Nanoclusters of Self-crowded Monoclonal Antibodies for Low Viscosity, Subcutaneous Injections.", Ph. D. Thesis. Department of Chemical Engineering. Austin, The University of Texas at Austin, May 2011, 328 pages.
Miller, M. A. et al., "Low Viscosity Highly Concentrated Injectable Nonaqueous Suspensions of Lysozyme Microparticles", Langmuir 2010, 26(2):1067-1074.
Office Action in Japanese Application No. JP 2010-513468, dated Mar. 28, 2013, 5 pages. (English Translation).
Office Action in Japanese Application No. JP 2011-536414, dated Dec. 17, 2013, 4 pages. (English Translation).
Overhoff et al. "Novel ultra-rapid freezing particle engineering process for enhancement of dissolution rates of poorly water-soluble drugs", European Journal of Pharmaceutics and Biopharmaceutics vol. 65, No. 1, Jan. 2007, pp. 55-67.
Rogers et al., "Solution Based Particule Formation of Pharmaceutical Powders by Supercritical or Compressed Fluid CO2 and Cryogenic Spray-Freezing Technologies", Drug Development and Industrial Pharmacy, 2001, 27(10):1003-1015.
Yu, Z. et al., "Spray freezing into liquid versus spray-freeze drying: Influence of atomization on protein aggregation and biological activity", European Journal of Pharmaceutical Sciences 2006, 27:9-18.
Aragon, S. et al. (2006). Biophysical Journal 91(5): 1591-1603.
Arakawa, T. et al. (2007). Biophysical chemistry 127(1-2): 1-8.
Asakura, S. et al. (1958), Journal of Polymer Science 33(126): 183-192.
Auton M. et al. (2005). "Predicting the energetics of osmolyte-induced protein folding/unfolding," Proc Natl Acad Sci U S A 102(42):15065-15068.
Baglioni, P. et al. (2004). Journal of Physics: Condensed Matter 16, (42), S5003-S5022.
Beenakker CWJ et al. (1984). "Diffusion of Spheres in a Concentrated Suspension," Physica A 126(3):349-370.
Carpenter, J. F. et al. (2009), Journal of Pharmaceutical Sciences 98(4): 1201-1205.
Carter, P. J. (2006). Nature Reviews Immunology 6(5): 343-357.
Chari, R., K. et al. (2009). Pharmaceutical Research 26(12): 2607-2618.
Chen, B. et al. (2003). Pharmaceutical Research 20(12): 1952-1960.
Chen, S. et al. (2009). Biomaterials 30(29): 5892-5896.

(56) References Cited

OTHER PUBLICATIONS

Cheung JK et al. (2005). "Coarse-Grained Strategy for Modeling Protein Stability in Concentrated Solutions," Biophysical journal 89(4):2372-2384.

Cheung MS et al. (2005). "Molecular Crowding Enhances Native State Stability and Refolding Rates of Globular Proteins," Proc Natl Acad Sci U S A 102(13):4753-4758.

Chi, E. Y. et al. (2003). Protein Science 12(5): 903-913.

Civera M. et al. (2005). "Unusual properties of aqueous solutions of L-proline: A molecular dynamics study," Chem Phys Lett 415(4-6):274-278.

Courtenay E.S. et al. (2000). "Vapor pressure osmometry studies of osmolyte-protein interactions: implications for the action of osmoprotectants in vivo and for the interpretation of osmotic stress experiments in vitro," Biochemistry 39(15):4455-4471.

Fersht, A. R. et al. (1993), Current Opinion in Structural Biology 3(1): 75-83.

Fields GB et al. (1992). "Theory for the Aggregation of Proteins and Copolymers," J Phys Chem 96(10):3974-3981.

Groenewold J et al. (2001). "Anomalously Large Equilibrium Clusters of Colloids," J Phys Chem B 105(47):11702-11709.

Groenewold J et al. (2004). "Colloidal Cluster Phases, Gelation and Nuclear Matter," J Phys-Condes Matter 16(42):S4877-S4886.

Hartl, FU et al. (2002). Science 295(5561):1852-1858.

Horn, F. M. et al. (2000). Journal of colloid and interface science 225(1):166-178.

Ignatova Z. et al. (2000). "Inhibition of protein aggregation in vitro and in vivo by a natural osmoprotectant," Proc Natl Acad Sci U S A 103(36):13357-13361.

Izutsu, K. et al. (1991), International Journal of Pharmaceutics 71(1-2): 137-146.

Kar K. et al. (2007). "Enhancement of thermal stability and inhibition of protein aggregation by osmolytic effect of hydroxyproline," Biopolymers 87(5-6):339-351.

Kreilgaard, L. et al. (1998). Archives of Biochemistry and Biophysics 360(1):121-134.

Kreilgaard, L. et al. (1999). Journal of Pharmaceutical Sciences 88(3): 281-290.

Lee, J. C. et al. (1981). Journal of Biological Chemistry 256:(14),:7193-7201.

Liu, W. et al. (2005). Biotechnology and bioengineering 90(4): 482-490.

Liu, J. et al. (2005). Journal of Pharmaceutical Sciences 94(9): 1928-1940.

Loewenthal, R. et al. (1992). Journal of Molecular Biology 224(3): 759-770.

Mehl, J. W. et al. (1940). Science 92(2380): 132-133.

Miao F. et al. (2009). "Theoretical analysis of excipient concentrations during the final ultrafiltration/diafiltration step of therapeutic antibody," Biotechnol Prog 25(4):964-972.

Miller D.P et al. (1997). "Thermophysical properties of trehalose and its concentrated aqueous solutions," Pharm Res 14(5):578-590.

Mutch, K. J. et al. (2006). Soft Matter 3(2):155-167.

Pilz I. et al. (1970). "Small Angle X-Ray Scattering of a Homogeneous GammaG1 Immunoglobin," Biochemistry 9(2):211-219.

Rosenbaum, D. et al. (1996). "Phase Behavior of Small Attractive Colloidal Particles," Phys Rev Let 76(1):150-153.

Rosenberg E, et al. (2009). "Ultrafiltration concentration of monoclonal antibody solutions: Development of an optimized method minimizing aggregation," Journal of Membrane Science 342(1-2):50-59.

Ross, P.D. et al. (1977). Biochemical and biophysical research communications 76(4):971-976.

Saito, S. et al. (2012). Pharm Res 29(2),:397-410.

Saluja, A. et al. (2008. International Journal of Pharmaceutics 358(1-2): 1-15.

Samuel D. et al. (2000). "Proline inhibits aggregation during protein refolding," Protein Sci 9(2):344-352.

Schneider, C. P. et al. (2009). Journal of Physical Chemistry B 113(7): 2050-2058.

Shen V.K. et al. (2006). "Coarse- Grained Strategy for Modeling Protein Stability in Concentrated Solutions II: Phase Behavior," Biophysical journal 90:1949-1960.

Shen, V. K. et al. (2009). Journal of biomechanical engineering 131(7): 071002-2, 7 pages.

Shire S.J. et al. (2004). Challenges in the Development of High Protein Concentration Formulations. J Pharm Sci 93(6):1390-1402.

Stoner M.R. et al. (2004). "Protein-solute interactions affect the outcome of ultrafiltration/diafiltration operations," Journal of pharmaceutical sciences 93(9):2332-2342.

Torquato S. et al. (2000). "Is Random Close Packing of Spheres Well Defined?" Phys Rev Lett 84(10):2064-2067.

Troitzsch R.Z. et al. (2008). "Molecular mechanisms of cryoprotection in aqueous proline: light scattering and molecular dynamics simulations," J Phys Chem B 112(14):4290-4297.

Tuinier, R. et al. (2003). Advances in Colloid and 20 Interface Science 2003, 103, 1-31.

Valente, J. J. et al. (2005). Biophysical Journal 89(6): 4211-4218.

Vondragek, J. et al. (2009). The Journal of Physical Chemistry B 113(27): 9041-9045.

Vrij, A. (1976). Pure and Applied Chemistry 48(4): 471-483.

Webb, S., S. Rule, et al. (1997), Pharmaceutical Research (New York) 14(11 Suppl.): S159.

Wolde, P.R et al. (1997). "Enhancement of Protein Crystal Nucleation by Critical Density Fluctuations," Science 277:1975-1978.

Xie G. et al. (1997). "The thermodynamic mechanism of protein stabilization by trehalose," Biophysical Chemistry 64:25-43.

Young T.M. et al. (2009). "Structure and Thermodynamics of Colloidal Protein Cluster Formation: Comparison of Square-Well and Simple Dipolar Models," The Journal of Chemical Physics 131(12):125104-1-125104-9.

Zaccarelli, E. (2007). "Colloidal Gels: Equilibrium and Non-Equilibrium Routes," J Phys: Condens Matter 19:323101, 51 pages.

Zhou H.X. et al. (2008). "Macromolecular Crowding and Confinement Biochemical, Biophysical, and Potential Physiological Consequences," Annual Review of Biophysics 37(1):375-397.

* cited by examiner

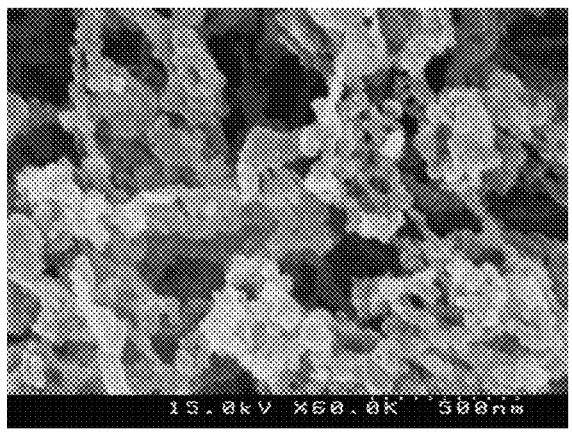
Fig. 10A
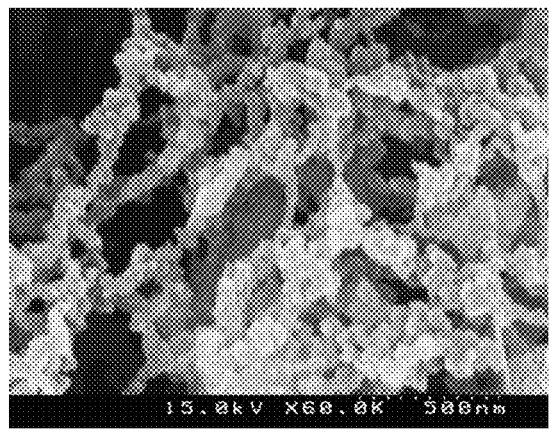
Fig. 10B
Fig. 11
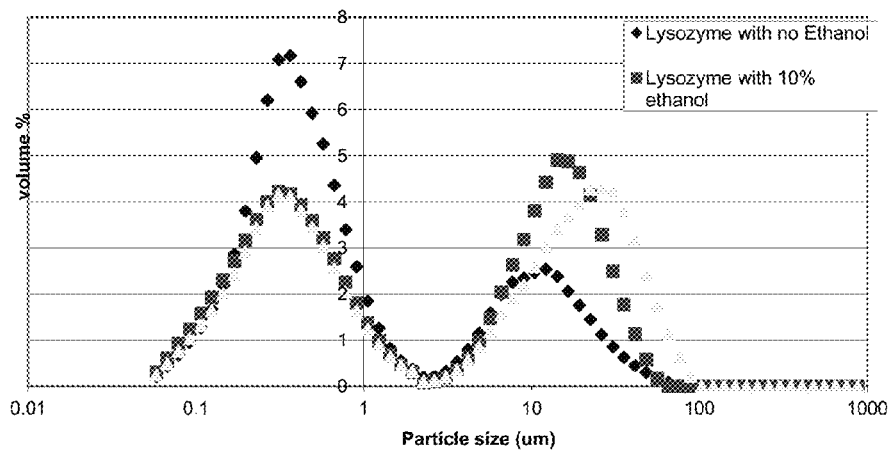
Fig. 12
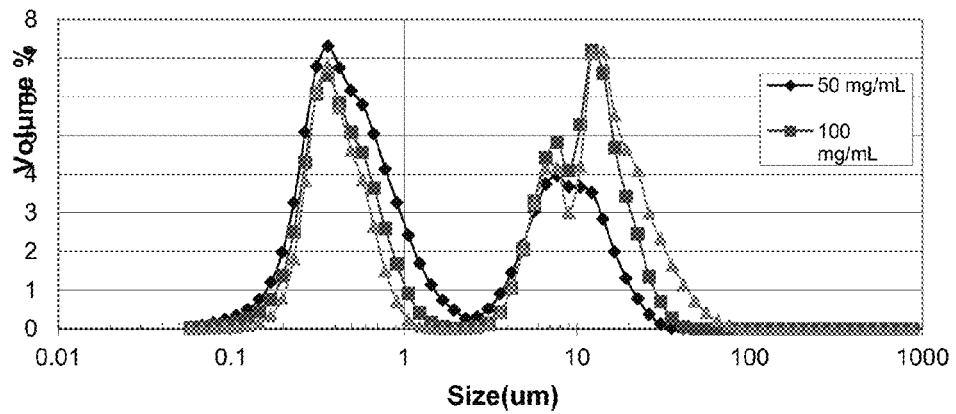

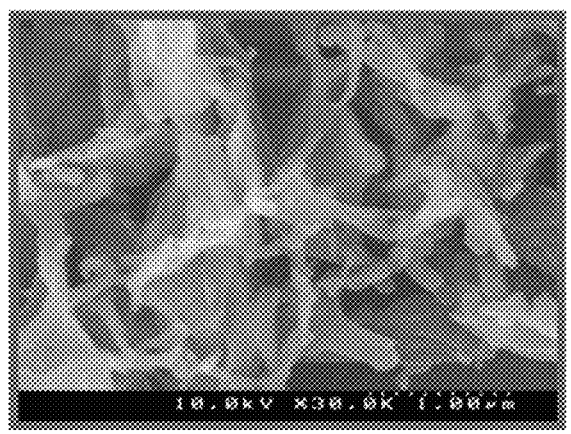
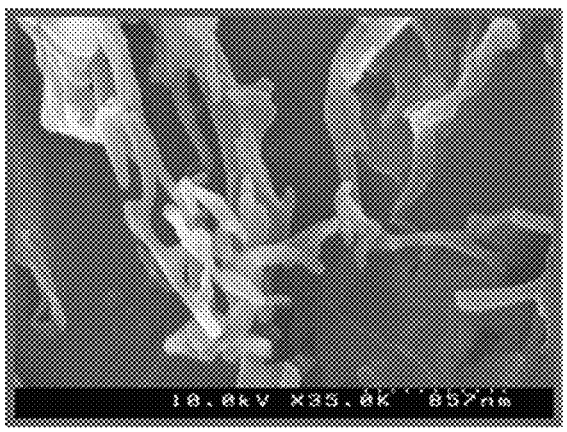
Fig. 13A          Fig. 13B
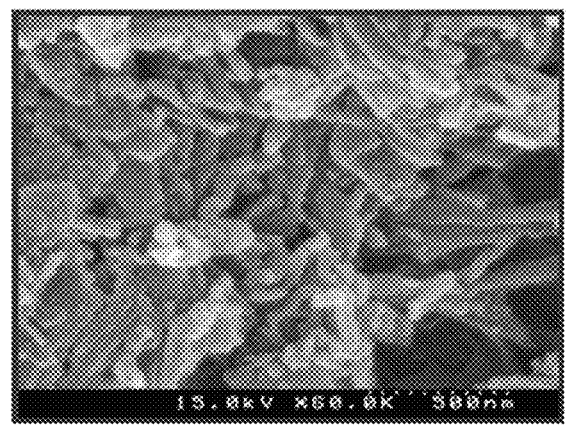
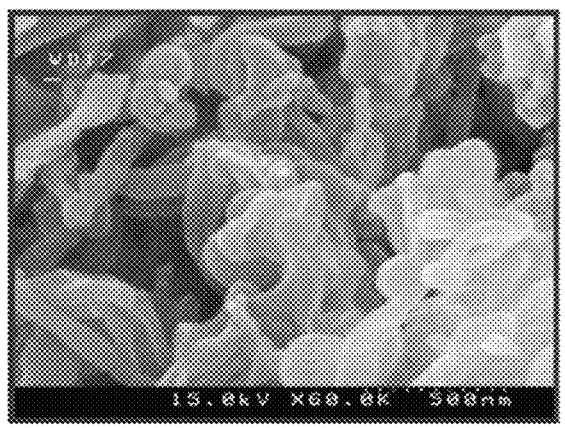
Fig. 13C          Fig. 13D
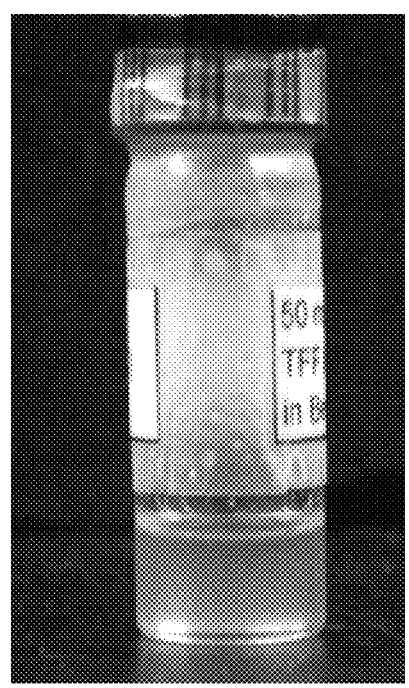
Fig. 14

FORMATION OF STABLE SUBMICRON PEPTIDE OR PROTEIN PARTICLES BY THIN FILM FREEZING

CROSS-REFERENCES TO RELATED APPLICATIONS

This application is a divisional of U.S. patent application Ser. No. 12/665,386, filed Jun. 2, 2010, which is a U.S. National Phase application under 37 U.S.C. §371 of International Application No. PCT/US2008/067766, filed Jun. 20, 2008, which in turn claims the benefit of U.S. Provisional Patent Application No. 60/945,737, filed Jun. 22, 2007, all of which are incorporated herein by reference in their entirety for all purposes.

STATEMENT AS TO FEDERALLY SPONSORED RESEARCH

This invention was made with government support under Grant No. AA-FG02-04ER15549 awarded by the Department of Energy. The government has certain rights in the invention.

TECHNICAL FIELD OF THE INVENTION

The present invention relates in general to the field of particle formation, and more particularly, to the formation of stable submicron protein particles.

BACKGROUND OF THE INVENTION

Without limiting the scope of the invention, its background is described in connection with methods to produce stable submicron peptide and protein particles.

For example, the U.S. Pat. No. 6,723,347 teaches a process for producing protein powder. The '347 patent describes a process for conveniently producing a stable protein powder retaining the higher-order structure at a high level which comprises freezing a protein-containing solution at a cooling rate of about −300 to −10° C./min. and then drying.

Another example can be found in U.S. Pat. No. 6,284,282, in which Maa et al. teach a method of spray freeze drying proteins for pharmaceutical administration. Maa's application relates to the spray freeze dry preparation of dry powder formulations of therapeutic proteins suitable for administration via pulmonary delivery.

Yet another example is found in U.S. Pat. No. 6,862,890 entitled "Process for Production of Nanoparticles and Microparticles by Spray Freezing into Liquid". The '890 patent provides a system and a method for the production of microparticles and nanoparticles of materials that can be dissolved. The system and method provide quicker freezing times, which in turn produces a more uniform distribution of particle sizes, smaller particles, particles with increased porosity and a more intimate mixing of the particle components. The system and method of the '890 patent also produce particles with greater surface area than conventional methods, and a method for the preparation of particles. An effective ingredient is mixed with water, one or more solvents, or a combination thereof, and the resulting mixture is sprayed through an insulating nozzle located at or below the level of a cryogenic liquid. The spray generates frozen particles.

Yet another example is shown in the U.S. Pat. No. 6,254,854 by Edwards et al. entitled "Porous particles for deep lung delivery". The '854 patent teaches improved porous particles for drug delivery to the pulmonary system, and methods for their synthesis and administration. The porous particles are made of a biodegradable material and have a mass density less than 0.4 g/cm$^3$. The particles may be formed of biodegradable materials such as biodegradable polymers. For example, the particles may be formed of a functionalized polyester graft copolymer consisting of a linear a hydroxy-acid polyester backbone having at least one amino acid group incorporated therein and at least one poly(amino acid) side chain extending from an amino acid group in the polyester backbone. Porous particles having a relatively large mean diameter, for example greater than 5 µm, can be used for enhanced delivery of a therapeutic agent to the alveolar region of the lung. The porous particles incorporating a therapeutic agent may be effectively aerosolized for administration to the respiratory tract to permit systemic or local delivery of wide variety of therapeutic agents.

Finally, U.S. Pat. No. 5,019,400 teaches a very low temperature casting of controlled release microspheres The '400 patent describes a process for preparing microspheres using very cold temperatures to freeze polymer-biologically active agent mixtures into polymeric microspheres with very high retention of biological activity and material. Polymer is dissolved in a solvent together with an active agent that can be either dissolved in the solvent or dispersed in the solvent in the form of microparticles. The polymer/active agent mixture is atomized into a vessel containing a liquid non-solvent, alone or frozen and overlayed with a liquified gas, at a temperature below the freezing point of the polymer/active agent solution. The cold liquified gas or liquid immediately freezes the polymer droplets. As the droplets and non-solvent for the polymer is warmed, the solvent in the droplets thaws and is extracted into the non-solvent, resulting in hardened microspheres.

A disadvantage of the above mentioned techniques when used with proteins and peptides is that it that proteins and peptides often form aggregates when the particle size becomes smaller than about 1 µm, because they are exposed to large vapor-liquid interfaces during water removal. These aggregates remain upon reconstitution in buffer. Therefore, such techniques may not lead to biologically active micronized protein powders.

Furthermore, it is difficult to control the particle size distribution in these processes in many cases. Methods are needed to remove water from solutions of peptides and proteins to produce small particles, with control of the size distribution, without forming protein aggregates.

SUMMARY OF THE INVENTION

The present inventors realized a need for a simple, efficient and robust process for freezing either small (<1 mL) quantities of protein solution or commercial quantities, that can produce stable submicron particles, e.g., protein particles.

More particularly, the present invention includes compositions and method for preparing micron-sized or submicron-sized particles by dissolving a water soluble effective ingredient in one or more solvents; spraying or dripping droplets solvent such that the effective ingredient is exposed to an vapor-liquid interface of less than 50, 100, 150, 200, 250, 300, 400 or even 500 cm$^{-1}$ area/volume; and contacting the droplet with a freezing surface that has a temperature differential of at least 30° C. between the droplet and the surface, wherein the surface freezes the droplet into a thin film with a thickness of less than 500 micrometers and a surface area to volume between 25 to 500 cm$^{-1}$. In one aspect, the method further includes the step of removing the solvent from the frozen material to form particles. In one aspect, the droplets freeze upon contact with the surface in about 50, 75, 100, 125, 150, 175, 200, 250, 500, 1,000 and 2,000 milliseconds. In another aspect, the droplets freeze upon contact with the surface in about 50 and 150 milliseconds. In another aspect, the droplet has a diameter between 2 and 5 mm at room temperature. In another aspect, the droplet forms a thin film on the surface of between 50 and 500 micrometers in thickness. In another aspect, the droplets have a cooling rate of between 50-250 K/s. In another aspect, the particles after solvent removal have a surface area of 10, 15, 25, 50, 75, 100, 125, 150 or 200 m$^2$/gr.

In one embodiment, the effective ingredient is a protein or peptide and the particle has less than 50% of the peptide or peptide or protein at the particle surface. The effective ingredient or active agent may a protein or peptide and the particle has less than 25, 15, 10 or 5% of the peptide or peptide or protein at the surface. In another aspect, the particles are submicron in diameter and may even include particle fibers less than one micron in diameter. In another aspect, the effective ingredient includes a surfactant peptide or peptide or protein, a DNase, and α-1-antitrypsin, an interleukin, a protease inhibitor, an interleukin receptor, a monoclonal antibody, a muramyl dipeptide, a catalase, a phosphatase, a kinase, a receptor antagonist, a receptor agonist, a dismutase, a calcitonin, a hormone, an interfereon, insulin, a growth factor, erythropoietin, heparin, vasopressin, peptides, albuterol sulfate, terbutaline sulfate, insulin, glucagon-like peptide, C-Peptide, erythropoietin, calcitonin, human growth hormone, leutenizing hormone, prolactin, adrenocorticotropic hormone, leuprolide, interferon α-2b, interferon beta-1a, sargramostim, aldesleukin, interferon α-2a, interferon alpha, n3 α-peptide or proteinase inhibitor; etidronate, nafarelin, chorionic gonadotropin, prostaglandin E2, epoprostenol, acarbose, metformin, or desmopressin, cyclodextrin, antibiotics; and the pharmacologically acceptable organic and inorganic salts or metal complex thereof.

In one embodiment, the surface is cooled by a cryogenic solid, a cryogenic gas, a cryogenic liquid or a heat transfer fluid capable of reaching cryogenic temperatures or temperatures below the freezing point of the solvent. In another aspect, the solvent further includes one or more excipients selected from sugars, phospholipids, surfactants, polymeric surfactants, vesicles, polymers, including copolymers and homopolymers and biopolymers, dispersion aids, and serum albumin. In another aspect, the effective ingredient includes an enzyme and the enzymatic activity of the enzyme is greater than 90%. In another aspect, the effective ingredient includes a peptide or protein and peptide or protein aggregation is less than 3%. In another aspect, the temperature differential between the droplet and the surface is at least 50° C.

The present invention also includes a pharmaceutical formulation that includes drug particles prepared by preparing micron-sized or submicron-sized particles by dissolving a water soluble effective ingredient or active agent in one or more solvents; spraying or dripping droplets solvent such that the effective ingredient is exposed to an vapor-liquid interface of less than 50 cm$^{-1}$ area/volume; and contacting the droplet with a freezing surface that has a temperature differential of at least 30° C. between the droplet and the surface, wherein the surface freezes the droplet into a thin film with a thickness of less than 500 micrometers and a surface area to volume between 25 to 500 cm$^{-1}$.

Another embodiment of the present invention includes a method for preparing micron-sized or submicron-sized solvent particles including: spraying or dripping droplets of a water soluble peptide or protein in a solvent, wherein the droplet is exposed to an vapor-liquid interface of less than 50 cm$^{-1}$ area/volume; contacting the droplet with a freezing surface that has a temperature differential of at least 30° C. between the droplet and the surface, wherein the droplet freezes into a thin film with a thickness of less than 500 micrometers and a surface area to volume between 25 to 500 cm$^{-1}$. The method may further include the step of removing the solvent from the frozen material to form particles. In another aspect, the solvent further includes at least one or more excipient or stabilizers selected from, e.g., sugars, phospholipids, surfactants, polymeric surfactants, vesicles, polymers, including copolymers and homopolymers and biopolymers, dispersion aids, and serum albumin. In another aspect, the peptide or protein includes an enzyme and the enzymatic activity of the enzyme is greater than 90%. In another aspect, the peptide or protein aggregation is less than 3%. In another aspect, the temperature differential between the solvent and the surface is at least 50° C. In another aspect, the particle has less than 50% of the peptide or protein at the surface. In another aspect, the particle has less than 25, 15, 10 or 5% of the peptide or protein at the surface. In another aspect, the peptide or protein includes, e.g., a surfactant peptide or protein, DNase, and α-1-antitrypsin, interleukin, interferon, protease inhibitor, interleukin receptor, monoclonal antibody, muramyl dipeptide, catalase, phosphatase, kinase, receptor antagonist, receptor agonist, dismutase, calcitonin, hormone, insulin, a growth factor, erythropoietin, heparin, vasopressin, peptides, glucagon-like peptide, C-Peptide, erythropoietin, human growth hormone, luteinizing hormone, prolactin, adrenocorticotropic hormone, leuprolide, interferon, interferon α-2b, interferon beta-1a, sargramostim, aldesleukin, interferon α-2a, interferon alpha, n3 α-peptide or proteinase inhibitor; and the pharmacologically acceptable organic and inorganic salts or metal complex thereof.

In one embodiment, the present invention includes a formulation, e.g., a pharmaceutical formulation or active agent, that includes drug particles prepared by preparing micron-sized or submicron-sized solvent particles including: spraying or dripping droplets of a water soluble peptide or protein in a solvent, wherein the droplet is exposed to an vapor-liquid interface of less than 50 cm$^{-1}$ area/volume; contacting the droplet with a freezing surface that has a temperature differential of at least 30° C. between the droplet and the surface, wherein the droplet freezes into a thin film with a thickness of less than 500 micrometers and a surface area to volume between 25 to 500 cm$^{-1}$.

Yet another embodiment includes compositions and methods for preparing micron-sized or submicron-sized particles by preparing an emulsion including a water soluble effective ingredient in solution; spraying or dripping droplets of the solution such that the effective ingredient is exposed to an vapor-liquid interface of less than 50 cm$^{-1}$ area/volume; and contacting the droplet with a freezing surface that has a temperature differential of at least 30° C. between the droplet and the surface, wherein the surface freezes the droplet into a thin film with a thickness of less than 500 micrometers and a surface area to volume between 25 to 500 cm$^{-1}$.

Yet another embodiment includes a system for preparing solvent nano and micro-particles that includes a solvent source composed of one or more solvents; a vessel containing a cryogenic liquid selected from cryogenic liquid selected from the group consisting of carbon dioxide, nitrogen, ethane, propane, helium, argon, or isopentane; and an insulating nozzle having an end and a tip, wherein the end of the nozzle is connected to the solvent source and the tip is placed above, at or below the level of the cryogenic liquid. In one aspect, the solution source further includes water, at least one organic solvent, or a combination thereof. In one aspect, the organic solvent is elected from the group consisting of ethanol, methanol, tetrahydrofuran, acetonitril acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

In another embodiment, a method for spray freezing including: spraying a solvent through an insulating nozzle located above, at or below the level of a cryogenic liquid, wherein the spray rapidly generates frozen solvent particles having a size range of 10 nm to 10 microns. In one aspect, the solvent particles produced have a particle size of less than 10 microns. In another aspect, the solvent particle has a surface area greater than 50 $m^2/g$. In one aspect, the cryogenic material is a liquid, a gas, a solid or a surface. In another aspect, the one or more solvents comprises a first solvent that is less volatile than a second solvent, wherein the more volatile solvent is removed but not the second solvent. In yet another aspect, the one or more solvents comprises a first solvent that is less volatile than a second solvent, wherein the more volatile solvent is removed by evaporation, lyophilization, vacuum, heat or chemically.

Yet another embodiment of the present invention includes a single-step, single-vial method for preparing micron-sized or submicron-sized particles by reducing the temperature of a vial wherein the vial has a temperature differential of at least 30° C. between the solvent and the vial and spraying or dripping solvent droplets of a water soluble effective ingredient dissolved in one or more solvents directly into the vial such that the effective ingredient is exposed to a vapor-liquid interface of less than 500 $cm^{-1}$ area/volume, wherein the surface freezes the droplet into a thin film with a thickness of less than 500 micrometers and a surface area to volume between 25 to 500 $cm^{-1}$. The droplets freeze may upon contact with the surface in about 50, 75, 100, 125, 150, 175, 200, 250, 500, 1,000 and 2,000 milliseconds, and may even freeze upon contact with the surface in about 50, 150 to 500 milliseconds. In one example, a droplet has a diameter between 0.1 and 5 mm at room temperature or even a diameter between 2 and 4 mm at room temperature. In another example, the droplet forms a thin film on the surface of between 50 and 500 micrometers in thickness. In one specific example the droplets will have a cooling rate of between 50-250 K/s. The vial may be cooled by a cryogenic solid, a cryogenic gas, a cryogenic liquid, a freezing fluid, a freezing gas, a freezing solid, a heat exchanger, or a heat transfer fluid capable of reaching cryogenic temperatures or temperatures below the freezing point of the solvent. The vial may even be rotated as the spraying or droplets are delivered to permit the layering or one or more layers of the final particles. In one example, the vial, the water soluble effective ingredient and the one or more solvents are pre-sterilized prior to spraying or dripping. The method may also include the step of spraying or dripping is repeated to overlay one or more thin films on top of each other to fill the vial to any desired level up to totally full.

BRIEF DESCRIPTION OF THE DRAWINGS

For a more complete understanding of the features and advantages of the present invention, reference is now made to the detailed description of the invention along with the accompanying figures and in which:

FIG. 10A is a SEM image of top of dried lysozyme thin film at the center.

FIG. 10B is a SEM image of top of dried lysozyme thin film at approximately 10 μm from the edge.

FIG. 11 is a graph that shows thin film freezing of lysozyme with various amounts of Ethanol in original Concentration Measured after 10 minutes of sonication by Malvern Mastersizer.

FIG. 12 is a graph that shows various high initial solubilized concentrations of lysozyme frozen by TFF and then lyophilized.

FIGS. 13A and 13 B shows the morphologies of TFF lysozyme prepared in glass vial (TFF lys: feed=5 mg/mL prepared directly in a glass vial) versus a TFF lysozyme prepared on a drum (FIGS. 13C to 13D) (TFF lys: feed=5 mg/mL prepared on TFF drum).

FIG. 14 shows the resuspended suspension of TFF particles in a suitable solvent for parenteral delivery.

DETAILED DESCRIPTION OF THE INVENTION

Figure 1A:
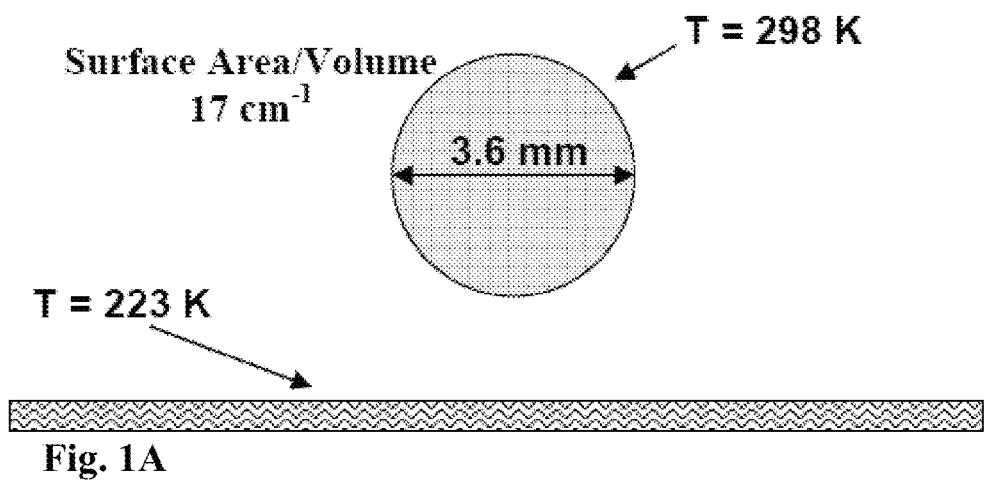
FIG. 1A is a diagram of the thin film freezing process displaying the falling droplet.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The ability to produce high surface area stable submicron and micron-sized protein particles would create new opportunities for oral, depot, pulmonary, and transdermal delivery applications (1-9). In pulmonary delivery, high surface area porous particles with aerodynamic diameters between 1-3 µm may be deposited more efficiently in the deep lung compared to dense particles with similar aerodynamic diameters (1, 8). In depot delivery, 300-500 nm submicron protein particles have been encapsulated uniformly into 10-50 µm diameter microspheres to achieve high protein loadings, while minimizing burst release (4, 6, 10, 11).

Solid protein particles, stabilized by cryoprotectants including sugars, are often less susceptible to destabilization during storage (1, 12-17) relative to proteins in solution. However, the formation of stable submicron protein particles with surface areas exceeding 10 $m^2/g$ (4, 18, 19) is highly challenging, as the removal of water exposes protein molecules to large interfacial areas. Adsorption of protein at gas-liquid and ice-liquid interfaces often results in unfolding and aggregation (1, 18-22). In lyophilization, the most common process for producing stable protein particles, particle growth during slow cooling (~1 K/min) limits the particle diameter to a minimum of a few microns with surface areas less than 1 $m^2/g$ (21). The same limitation is true when drop freezing small aliquots (~20-50 μL) of protein solution into liquid nitrogen (23), freezing thick (>500 μm) films on a cooled shelf (24), and plunge freezing ultra-thin walled PCR tubes filled with protein solution into liquid nitrogen (23). In these techniques, the protein solution was cooled at rates between 1 to 10 K/s (23, 24). Although the dried particles may be milled to form submicron particles, yields can be limited, size distributions are often broad, and the mechanical stress can lead to denaturation (1, 21). Submicron protein particles may be precipitated from aqueous solution by a variety of processes including spray-drying (11, 21, 22, 25), supercritical $CO_2$-assisted aerosolization and bubble drying (sc$CO_2$A-BD) (26), spray freeze-drying (SFD) (1, 18, 19, 21), and spray freezing into liquids (SFL).

As used herein, "bioavailability" is a term meaning the degree to which a drug becomes available to the target tissue after being administered to the body. Poor bioavailability is a significant problem encountered in the development of pharmaceutical compositions, particularly those containing an active ingredient that is not highly soluble in water. In certain embodiments, the proteins may be water soluble, poorly soluble, not highly soluble or not soluble. The skilled artisan will recognize that various methodologies may be used to increase the solubility of proteins, e.g., use of different solvents, excipients, carriers, formation of fusion proteins, targeted manipulation of the amino acid sequence, glycosylation, lipidation, degradation, combination with one or more salts and the addition of various salts.

As used herein, the term "effective ingredient" refers to a compound or compounds, whether in pure or partially purified form (e.g., extracts) that has an known effect on target. For example, pharmaceutical agents are effective ingredients for their known target, e.g., penicillin is an effective ingredient or agent against susceptible bacteria. Another example of an effective ingredient is an insecticide that has a known insect target. The present invention may be used to manufacture and delivery effective ingredients against targets in a manner that will enhance its delivery, as specifically described hereinbelow.

As used herein, "pharmaceutically acceptable carrier" includes any and all solvents, dispersion media, coatings, antibacterial and antifungal agents, isotonic and absorption delaying agents. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Particle formation technologies may be classified as either mechanical micronization processes or solution-based phase separation processes. Mechanical micronization methods include milling techniques such as that cited in U.S. Pat. No. 5,145,684. However, friction generated during these milling processes may lead to either thermal or mechanical degradation of the active pharmaceutical ingredient. Spray drying, another common method used to micronize drug substances, requires extremely high temperatures, on the order of 150° C., to remove the solvent from the drug following atomization. The elevated temperatures may accelerate degradation of the active ingredient.

Non-limiting examples of effective ingredients are pharmaceuticals, pharmaceutical agents, peptides, nucleic acids, proteins, antibiotics, gene therapy agents, catalysts, adsorbents, pigments, coatings, personal care products, abrasives, particles for sensors, metals, alloys, ceramics, membrane materials, nutritional substances, anti-cancer agents, as well as, chemicals used in the agriculture industries such as fertilizers, pesticides and herbicides. It will be appreciated that this list is not exhaustive and is for demonstrative purposes only. It will be further appreciated that it is possible for one compound to be included in more than one class of effective ingredients, for example, peptides and pharmaceuticals.

Examples of effective ingredients that are pharmaceutical agents include, but are not limited to, antibiotics, analgesics, anticonvulsants; antidiabetic agents, antifungal agents, antineoplastic agents, antiparkinsonian agents, antirheumatic agents, appetite suppressants, biological response modifiers, cardiovascular agents, central nervous system stimulants, contraceptive agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents. Further examples of effective ingredients include a cardiovascular drug, respiratory drug, sympathomimetic drug, cholinomimetic drug, adrenergic or adrenergic neuron blocking drug, antidepressant, antihypertensive agent, anti-inflammatory, antianxiety agent, immunosuppressive agents, antimigraine agents, sedatives/hypnotic, antianginal agents, antipsychotic agents, antimanic agents, antiarrhythmic, antiarthritic agent, antigout agents, anticoagulant, thrombolytic agents, antifibrinolytic agents, hemorheologic agents, antiplatelet agents, anticonvulsant, antihistamine/antipruritic, agent useful for calcium regulation, antiviral agents, anti-infective, bronchodialator, hormone, hypoglycemic agent, hypolipidemic agent, protein, nucleic acid, agent useful for erythropoiesis stimulation, antiulcer/antireflux agent, antinauseant/antiemetic, oil-soluble vitamin, mitotane, visadine, halonitrosourea, anthrocycline or ellipticine.

The pharmaceutical effective ingredients may be used in a variety of application modalities, including oral delivery as tablets, capsules or suspensions; pulmonary and nasal delivery; topical delivery as emulsions, ointments or creams; and parenteral delivery as suspensions, microemulsions or depot. The resulting powder can be redispersed at any convenient time into a suitable aqueous medium such as saline, buffered saline, water, buffered aqueous media, solutions of amino acids, solutions of vitamins, solutions of carbohydrates, or the like, as well as combinations of any two or more thereof, to obtain a suspension that can be administered to mammals.

The solution agent used in the solution can be an aqueous such as water, one or more organic solvents, or a combination thereof. When used, the organic solvents can be water soluble or non-water soluble. Suitable organic solvents include but are not limited to ethanol, methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

The excipients and adjuvants that may be used in the present invention, while potentially having some activity in their own right, for example, antioxidants, are generally defined for this application as compounds that enhance the efficiency and/or efficacy of the effective ingredients. It is also possible to have more than one effective ingredient in a given solution, so that the particles formed contain more than one effective ingredient.

As stated, excipients and adjuvants may be used to enhance the efficacy and efficiency of the effective ingredients. Non-limiting examples of compounds that can be included in the solutions that are to be spray frozen in accordance with the present invention include: cryoprotectants, lyoprotectants, surfactants, fillers, stabilizers, polymers, protease inhibitors, antioxidants and absorption enhancers. The excipients may be chosen to modify the intended function of the effective ingredient by improving flow, or bio-availability, or to control or delay the release of the effective ingredient. Specific nonlimiting examples include: sucrose, trehaolose, Span 80, Tween 80, Brij 35, Brij 98, Pluronic, sucroester 7, sucroester 11, sucroester 15, sodium lauryl sulfate, oleic acid, laureth-9, laureth-8, lauric acid, vitamin E TPGS, Gelucire 50/13, Gelucire 53/10, Labrafil, dipalmitoyl phosphadityl choline, glycolic acid and salts, deoxycholic acid and salts, sodium fusidate, cyclodextrins, polyethylene glycols, labrasol, polyvinyl alcohols, polyvinyl pyrrolidones and tyloxapol. Using the process of the present invention, the morphology of the effective ingredients can be modified, resulting in highly porous microparticles and nanoparticles.

Figure 1B:
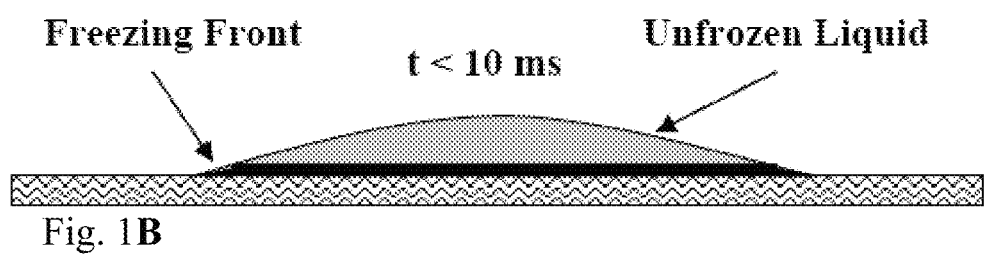
FIG. 1B is a diagram of falling droplet spreading after impact on the stainless steel surface.
Figure 1C:
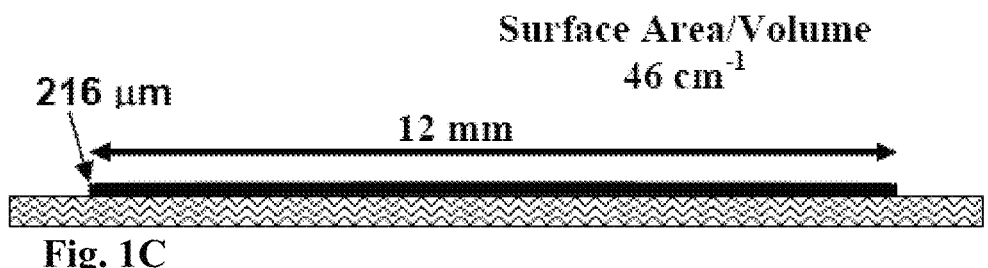
FIG. 1C is a diagram of a droplet during cooling and freezing as a thin film.

In certain embodiments, the present invention demonstrates a novel method to produce stable submicron protein particles. The method is herein referred to as thin film freezing (TFF). FIG. 1 illustrates one embodiment of TFF. In TFF, liquid droplets typically fall from a given height and impact, spread, and freeze on a cooled solid substrate. In FIG. 1A, a droplet 10 falls from a given height, and impact a spinning surface 12 that has a temperature of 223 K. As the droplet spreads out, freezing front 14 is formed in advance of the unfrozen liquid 16 shown in FIG. 1B. Typically, the size of the completely frozen droplet 18 is about 12 mm in diameter, with a height approximately 216 μm. Recently, TFF was used to form high SSA powder (25-29 $m^2$/g) of the poorly water soluble drug danazol (45). Liquid droplets (~2-4 mm in diameter) were dispensed from a pipette above a cryogenically cooled metal surface (46, 47). Upon impact, the droplets spread out into thin films (~100-400 μm) that froze on time scales of 70 to 1000 ms, which corresponds to a cooling rate of ~$10^2$ K/s (42-44, 47-57). The cooling rates predicted with a 1-D heat transfer model were in agreement with laboratory measurements with an infrared (IR) camera (45). Since the cooling rates in TFF and SFL are comparable, TFF may be expected to be a desirable process for forming high surface area protein particles.

As will be apparent to those of skill in the art, the droplets may be delivered to the cold or freezing surface in a variety of manners and configurations. For example, to provide for high-throughput capabilities, the droplets may be delivered in parallel, in series, at the center, middle or periphery or a platen, platter, plate, roller, conveyor surface. The freezing or cold surface may be a roller, a belt, a solid surface, circular, cylindrical, conical, oval and the like that permit for the droplet to freeze. For a continuous process a belt, platen, plate or roller may be particularly useful. In operation, frozen droplets may form beads, strings, films or lines of frozen substrate and effective ingredient that are removed from the surface with a scraper, wire, ultrasound or other mechanical separator prior to the lyophilization process. Once the material is removed from the surface of the belt, platen, roller or plate the surface is free to receive additional material in a continuous process.

In certain embodiments, the present invention demonstrate submicron LDH and lysozyme particles (>10 m$^2$/g) with 100% enzyme activity may be formed with TFF followed by lyophilization. The cooling rate was designed to be sufficiently fast to arrest particle growth, whereas the relatively small liquid-gas interfacial surface area helps prevent protein adsorption, unfolding and aggregation. The present invention presents dimensions of the thin films, stabilities (enzyme activity) of LDH powders after reconstitution, and morphologies of lysozyme particles determined by SEM and BET measurements of surface area. The present invention also gives cooling rates of the thin films determined by a 1-D heat transfer model and IR measurement. The cooling rates, particle morphologies and protein stabilities for the intermediate cooling rate processes TFF and SFL, relative to the ultra-rapid cooling process, SFD, and in the slow process, lyophilization were also compared. A protein nucleation and growth mechanism is presented to illustrate the particle morphologies in terms of the cooling rates. In TFF, the much smaller area of the gas-liquid interface of the falling droplet and spread film relative to the atomized droplets in SFD is shown to result in significantly less protein adsorption, and consequently, minimal denaturation and aggregation. Furthermore, the intermediate cooling rate (~10$^2$ K/s) is shown to be sufficient to arrest particle growth to give surface areas >30 m$^2$/g.

Compared to SFD and SFL, TFF offers the advantage of simplification in the processing steps, in addition to improvement in the stability of the protein. TFF on a cold metal surface bypasses the need to maintain aseptic conditions of a liquid cryogen, for example liquid nitrogen, in the SFD and SFL processes (24). The cooling rate of the thin films in TFF may be controlled readily by varying the temperature of the metal surface. Also, the surface temperature of the film may be measured directly (45). For SFL and SFD, the complex geometry of the turbulent spray in the liquid nitrogen (LN$_2$) combined with the Leidenfrost effect can be somewhat difficult to control and monitor (36). In TFF, more concentrated and thus more viscous solutions may be processed, as the droplets do not need to be atomized. In TFF, collection of the frozen films leads to nearly 100% yields. However, in SFD process yields were only about 80% as the result of entrainment of uncaptured particles in the atomized aqueous stream, particles sticking to the sides of collection vessels, and inefficient separation of the cryogen from the 10-100 μm frozen particles (11, 21).

Materials. Lysozyme was purchased from Sigma and L-LDH from porcine heart suspended in a 3.2 M ammonium sulfate solution from Roche Applied Science. Trehalose, NADH and pyruvate were purchased from Sigma. The water was deionized by flowing distilled water through a series of 2×7 L mixed bed vessels (Water and Power Technologies) containing 60:40 anionic:cationic resin blends.

LDH Enzyme preparation and catalytic activity assay. The LDH enzyme preparation and catalytic activity assay used in the present invention is described in detail in a previous reference (32). The LDH in ammonium sulfate was dialyzed against 10 mM KPO4 buffer (pH 7.5) at 4° C. for 3 hours before use (58, 59). LDH activities were measured for the reaction of pyruvate and NADH into lactate and NAD+. Units of LDH activity (U) were calculated by measuring the decrease in absorbance of NADH at λ=340 nm every 15 seconds for 1 minute due to the conversion of NADH to NAD over time (U=Δμmol NADH/min) and then dividing by the mass (mg) of the LDH protein in solution to determine specific activity (U/mg). The stability of the LDH formulation in 30 mg/mL trehalose was measured over time. The LDH specific activity remained stable for an hour and then began to decrease. All results were performed in the time period where the LDH specific activity had not decayed. During this time period, the specific activity was defined as 100%.

Example of the Thin Film Freezing (TFF) procedure. Aqueous protein solutions of LDH or lysozyme were passed at a flow rate of 4 mL/min either through a 17 gauge (1.1 mm ID, 1.5 mm OD) stainless steel syringe needle producing 3.6 mm diameter droplets or through 3.9 mm ID, 6.4 mm OD stainless steel tubing producing 5.6 mm diameter droplets. The droplets fell from a height of 10 cm above a rotating stainless steel drum 17 cm long and 12 cm in diameter. The stainless steel drum was hollow with 0.7 cm thick walls and was filled with dry ice or liquid nitrogen to maintain drum surface temperatures of 223 K or 133 K, respectively. Before each run, the surface temperature of the drum was verified with a DiGi-Sense® Type K thermometer using a 45° angle surface probe thermocouple attachment (Eutech Instruments). The drum rotated at approximately 12 rpm and was powered by a Heidolph RZR2041 mechanical overhead stirrer (ESSLAB) connected to a speed reducer. On impact the droplets deformed into thin films (FIG. 1) and froze. The frozen thin films were removed from the drum by a stainless steel blade mounted along the rotating drum surface. The frozen thin films then fell 5 cm into a 400 mL Pyrex® beaker filled with liquid nitrogen. For lysozyme, the frozen thin films in the 400 mL Pyrex® beakers were transferred directly to a −80° C. freezer to evaporate excess liquid nitrogen. For LDH, the frozen thin films were transferred from the 400 mL Pyrex® beakers into 50 mL polypropylene tubes (Part No. UP2255, United Laboratory Plastics) 2 cm in diameter and 16 cm in height using a spatula pre-cooled in liquid nitrogen.

Infrared Imaging of Cooling Thin Films. An InSb focal plane array (FPA) camera (Phoenix digital acquisition system (DAS camera, Indigo Systems) was positioned to acquire infrared images from above the cooling thin film on a flat plate. The FPA camera detected 3-5 μm radiation, and the images were acquired at 100 frames per second (10 ms/image). The dimensions of each frame were 256 pixels by 256 pixels (15 mm×15 mm). The image spatial resolution was approximately 40 μm per pixel. Average intensity values were calculated using MATLAB® version 6 (20×20 pixel square within the center of the droplet) and plotted versus time to determine the time for the center of the thin film to reach thermal equilibrium with the plate.

Drying and shelf loading. A Virtis Advantage Lyophilizer (The Virtis Company, Inc.) was used to dry the frozen slurries. The 400 mL beakers containing frozen slurries of lysozyme and the 50 mL polypropylene tubes containing the frozen slurries of LDH were covered with a single layer Kim-wipe. Primary drying was carried out at −40° C. for 36 hrs at 300 mTorr and secondary drying at 25° C. for 24 hrs at 100 mTorr. A 12 hour linear ramp of the shelf temperature from −40° C. to +25° C. was used at 100 mTorr.

LDH reconstitution and concentration assay. Dried LDH powders were reconstituted with 1 mL of DI water and the enzyme assay was performed immediately. After all protein samples had been analyzed for enzymatic activity, the protein concentration was measured with the BCA (bicinchoninic acid) protein analysis kit (Sigma Chemical Company). Once protein concentrations were determined, the specific activity from each measurement could be calculated. The activity of each LDH sample was normalized by the specific activity of the control measured immediately before the freezing process.

Transfer and storage of dried powders. After the lyophilization cycle was complete, the lyophilizer was purged with nitrogen upon releasing the vacuum to reduce the exposure time of the protein powders to water vapor in the ambient air before transfer. The samples were then rapidly transferred to a dry box held at 14% RH, and the powders were transferred to 20 mL scintillation vials. The vials were then covered with 24 mm Teflon® Faced Silicone septa (Wheaton) which were held in place by open-top screw cap lids. Vials were purged with dry nitrogen for 2 minutes via a needle through the septa and an additional needle for the gas effluent.

Surface area measurement. Surface areas of dried powders were measured with a Quantachrome Nova 2000 (Quantachrome Corporation) BET apparatus. Dried powders were transferred to the glass BET sample cells in a dry box. Samples were then degassed under vacuum for a minimum of 12 hours. The Brunauer, Emmett, and Teller (BET) equation (60) was used to fit adsorption data of nitrogen at 77 K over a relative pressure range of 0.05-0.30. The samples were measured two times.

Residual moisture content. Aliquots of methanol were dispensed through the septum of the scintillation vials to form a suspension concentration of 10-100 mg/mL. Vials were then placed in a bath sonicator (Mettler Electronics) for 5 minutes at maximum power to insure complete suspension of the powder. Moisture content was measured for a 200 µL aliquot with an Aquatest 8 Karl-Fischer Titrator (Photovolt Instruments). The moisture values were corrected with a 200 µL methanol blank control. All samples had a moisture content between 6-8% (w/w) after drying, comparable to values of 2-7% (w/w) for BSA prepared by SFD (18).

Particle size analysis. The size distribution of dried powders was measured by multiangle laser light scattering with a Malvern Mastersizer-S (Malvern Instruments). A mass of 30-100 mg of powder was suspended in 10 mL of acetonitrile and the suspension was then sonicated on ice for 1 minute using a Branson Sonifier 450 (Branson Ultrasonics Corporation) with a 102 converter and tip operated in pulse mode at 35 W. Typical obscuration values ranged from 11% to 13%. Aliquots of the sonicated suspension were then dispensed into a 500 mL acetonitrile bath for analysis.

Scanning electron microscopy (SEM). SEM images were collected on a Hitachi Model S-4500 scanning electron microscope (Hitachi Ltd). The samples were prepared in a dry-box. Aluminum stages fitted with double adhesive carbon conducting tape were gently dipped into sample vials until covered by powder. Stages were then placed in septum capped vials and purged with nitrogen for transfer. To minimize the time samples were exposed to atmospheric moisture the stages were rapidly transferred to a Pelco Model 3 sputter-coater. A conductive gold layer was applied and the samples were then quickly transferred to the SEM. Total exposure to the atmosphere was less than 1 minute.

Table 1 (below) shows the characterization of thin films formed from deionized water droplets as a function of surface temperature and droplet diameter.

TABLE 1

|  | SFD[a] | SFL[a] | Thin Film from 3.6 mm Drop[b] | | Thin Film from 5.6 mm Drop[c] | |
| --- | --- | --- | --- | --- | --- | --- |
|  |  |  | 223 K[d] | 133 K[d] | 223 K[d] | 133 K[d] |
| Droplet or Thin Film Disk Diameter (µm) | 10 | 100 | 12000 | 10000 | 23000 | 19000 |
| Film Thickness (µm) | — | — | 216 | 311 | 221 | 324 |
| Droplet or Thin Film Surface Area to Volume (cm$^{-1}$) | 6000 | 600 | 46 | 32 | 45 | 31 |

[a]Values taken from Engstrom et al. (36)
[b]Surface Area to Volume of 3.6 mm droplet is 17 cm$^{-1}$
[c]Surface Area to Volume of 5.6 mm droplet is 11 cm$^{-1}$
[d]Temperatures of stainless steel plate The droplets spread on the cold metal surface and formed a cylindrical thin disk. The disk diameter decreased with a decrease in surface temperature from 223 K to 133 K and increased with an increase in falling droplet radius. Since the frozen thin films were cylindrical disks, the thicknesses of the thin films were calculated from the known volume of the liquid droplet and the measured disk diameter. The volumes of the falling droplets were determined by counting the number of droplets required to occupy 1 mL in a graduated cylinder. The average thin film thickness for the 223 K and 133 K surfaces were 220 µm and 320 µm, respectively. The corresponding surface area/volume ratios for the top surfaces of the cylinders are also shown in Table 1. The film thicknesses were essentially independent of the falling droplet diameter. For aqueous samples containing concentrations of lysozyme between 5 and 50 mg/mL or trehalose at 30 mg/mL, the droplet volumes, disk diameters, and thus film thicknesses did not change relative to pure water. The surface area/volume ratios for the 3.6 mm and 5.6 mm falling droplets in TFF were 17 cm$^{-1}$ and 11 cm$^{-1}$, respectively. As shown in Table 1, upon impact, the falling droplets spread into thin films with final surface area/volume ratios between 31 and 46 cm$^{-1}$. In a previous reference (36) of SFD and SFL, the corresponding surface area/volume ratios were 6000 and 600 cm$^{-1}$, respectively. Relative to these values, the much smaller surface area/volume ratio for TFF may be expected to lower the degree of protein destabilization from exposure to the gas-liquid interface.

The thin films were further characterized by determining the cooling rates from infrared measurements. The IR camera outputs intensity values with white indicating a high intensity and black a low intensity in relation to the amount of radiant energy E (energy density per unit time per unit wavelength) emitted from the droplet (45, 61). The radiant energy E is related to the temperature of the object according to Planck's law as equation (1)

$$E(\lambda,T)=(2\pi hc^2)/\{\lambda^5[\exp(hc/\lambda kT)-1]\} \quad \text{Equation (1)}$$

where $\lambda$ is the wavelength, c is the speed of light, k is the Boltzmann constant, h is Planck's constant and T is the temperature in Kelvin (61). Therefore, the intensity output of the IR camera is related directly to the temperature.

Figure 2A:
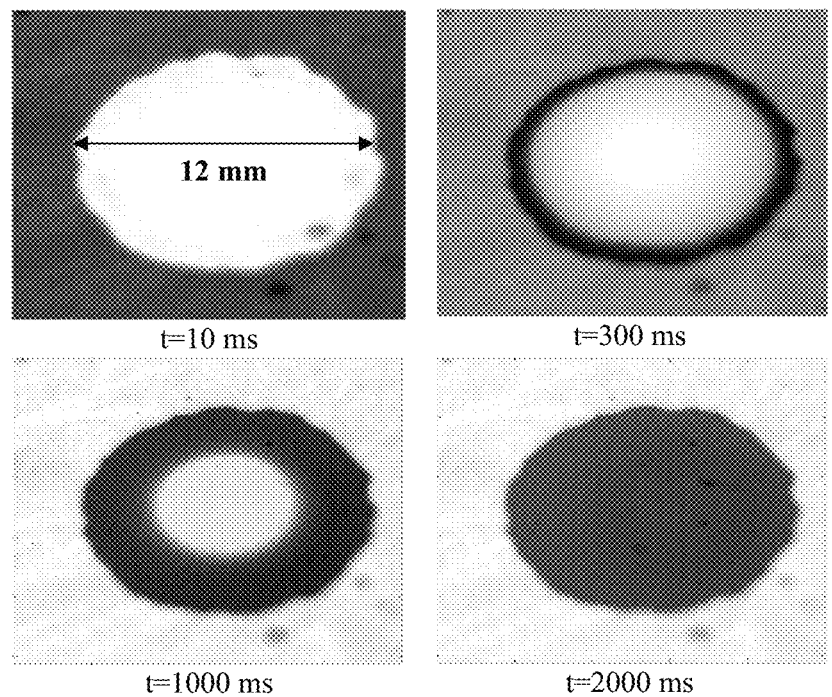
FIGS. 2A and 2B are infrared (IR) photographs of an aqueous droplet impinging and freezing on a stainless steel surface at 223 K and at 133K, respectively.
Figure 2B:
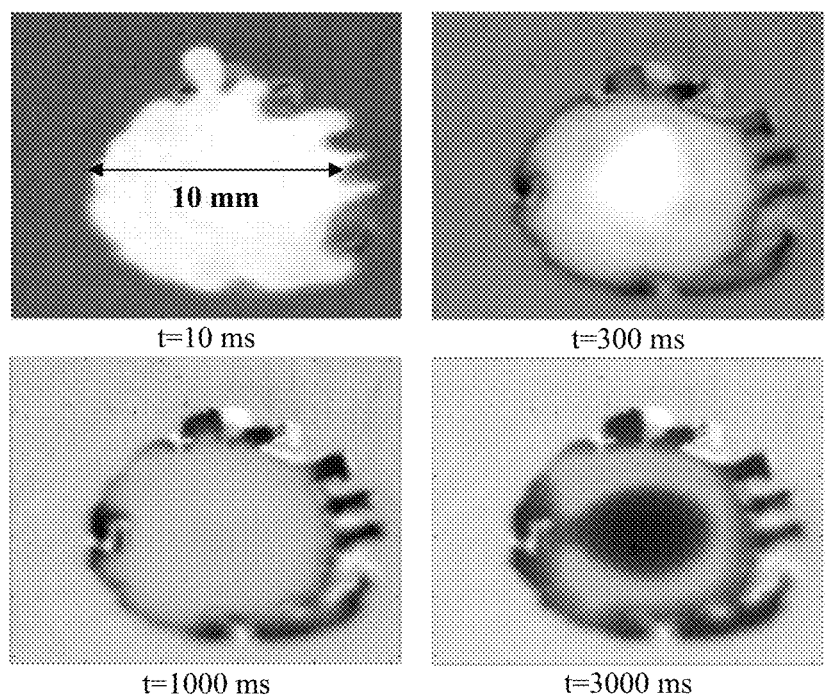
Figure 3:
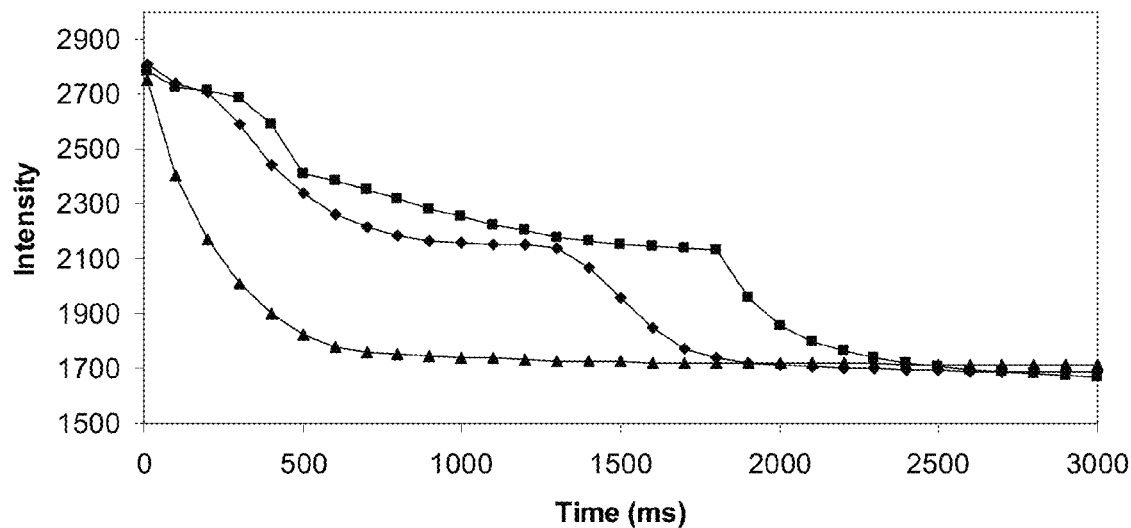
FIG. 3 is a plot of IR intensity versus time for an aqueous thin film on stainless steel surface at 223 K.

For the thin film on the 223 K surface shown in FIG. 2A, the diameter of the film was 12 mm and the edge was uniform and smooth. As cooling progressed, a cooling front moved radially inward from the edge of the film toward the center. The center of the film reached thermal equilibrium in 1.6 s shown in FIG. 2A and FIG. 3. For the thin film on the 133 K surface demonstrated in FIG. 2B, the diameter was 10 mm and dark jagged "fingers" were observed at the edge, indicating the coldest domains. The cooling front moved radially inward from the edge to the center at first. Next, the center turned black, and an annular region between the center and the outer jagged edge remained gray. The cooling front then reversed direction by moving from the center toward the edge of the film. FIG. 3 shows the center of the film reached thermal equilibrium a little more slowly, in about 3 s, relative to 223 K. In each case at the center of the film, a plateau was observed and then an abrupt final decay to thermal equilibrium.

The LDH activities for an aqueous formulation of 0.25 mg/mL LDH with 30 mg/mL trehalose frozen by lyophilization, SFL (32), and TFF were extremely high and not significantly different (p<0.05) according to a Student's t test shown in Table 2. Table 2 shows activities for 0.25 mg/mL LDH, 30 mg/mL trehalose formulations frozen by various techniques in pH 7.5, 10 mM $KPO_4$ buffer in replicates of 3.

TABLE 2

| | % Activity | |
|---|---|---|
| Freezing Process | 223 K | 133 K |
| Thin Film (3.6 mm drop) | 100 ± 3.9 | 104 ± 12.0 |
| Thin Film (5.6 mm drop) | 97 ± 9.5 | 100 ± 8.4 |
| SFL[a,d] | | 98 ± 5.3 |
| SFD-130 μm[a] | | 85 ± 8.2 |
| SFD-40 μm[a,e] | | 74 ± 6.7 |
| SFD-10 μm[a,d] | | 80 ± 5.4 |
| Falling Droplet (3.6 mm)[c] | | 98 ± 2.1 |
| Spray into Air (10 μm)[a,b,c] | | 85 ± 7.7 |
| Lyophilization | | 99 ± 2.1 |

[a]Values taken from Engstrom et al. (32)
[b]100 mg/mL trehalose used in LDH formulation
[c]The droplets were not frozen in these two controls
[d]Replicate of 4
[e]Replicate of 5

Compared to the SFD process for three droplet sizes, the LDH activities for each TFF condition were significantly higher (p<0.05). The very high LDH activities were maintained in the TFF process throughout the serial stresses of droplet falling and spreading, freezing, drying, and reconstitution.

Given the high enzyme activities for LDH particles formed by TFF, the other key goal was to demonstrate particle morphologies with submicron particle sizes and large particle surface areas. Table 3 demonstrates specific surface area measurements and particle size distributions for lysozyme powders formed by thin film freezing, SFL, and SFD.

TABLE 3

| | Lysozyme Concentration | SSA ($m^2/g$) | | Size (μm) | |
|---|---|---|---|---|---|
| Freeze Process | (mg/mL) | 223 K[a] | 133 K[a] | 223 K[a] | 133 K[a] |
| Thin Film (3.6 mm drop) | 5 | 73 ± 0.8 | 45 ± 0.4 | 0.050-1.0 (88%) 1.0-10 (12%) | 0.050-1.0 (81%) 1.0-12 (19%) |
| Thin Film (5.6 mm drop) | 5 | — | — | 0.050-1.0 (92%) 1.0-12 (8%) | 0.050-1.0 (84%) 1.0-10 (16%) |
| Thin Film (3.6 mm drop) | 50 | 31 ± 0.1 | 55 ± 0.4 | 0.050-1.0 (66%) 1.0-30 (34%) | 0.050-1.0 (62%) 1.0-30 (38%) |
| SFL[b] | 5 | 114 ± 11 | | 0.050-1.0 (85%) 2.0-10 (15%) | |
| SFL[b] | 50 | 34 ± 2 | | 0.050-1.0 (48%) 4.0-12 (52%) | |
| SFD-10 μm[b] | 50 | 126 ± 5 | | 0.050-1.0 (74%) 1.0-10 (26%) | |
| Lyophilization | 5 | 4.4 ± 0.2 | | 0.05-1.0 (7%) 4.8-120 (93%) | |

[a]Temperatures of stainless steel plate
[b]Values taken from Engstrom et al. (36)

In the case of LDH, the ratio of LDH:trehalose was 1:120 by mass. As discussed previously (32, 36), the particle surface area for trehalose decreased upon exposure to atmospheric moisture which lowers the Tg sharply. (This limitation may be overcome in the future with the use of lyostoppers to seal the vials from moisture.) Thus, we chose lysozyme as a model protein to investigate powder morphology instead of LDH:trehalose. Lysozyme samples obtained and transferred at room temperature had moisture contents between 6-8% as determined by Karl Fischer titration. For moisture contents between 7-8% by weight, the Tg remained high, between 50-60° C. (62). Therefore the loss in lysozyme SSA during transfer may be expected to be negligible. For most cases, the SSA values were similar ranging between 30 and 55 $m^2/g$. For 5 mg/mL lysozyme, the thinner films at 223 K produced a significantly higher SSA of 73 $m^2/g$ relative to the films at 133 K. In a previous reference (36), 5 and 50 mg/mL lysozyme solutions processed by SFL had measured powder SSAs of 114 $m^2/g$ and 34 $m^2/g$, respectively, similar to the values produced by TFF (36). Although the SSA of 126 $m^2/g$ for SFD was about 2 fold larger than for TFF, the enzyme activity was much smaller, as shown in Table 2.

Figure 4:
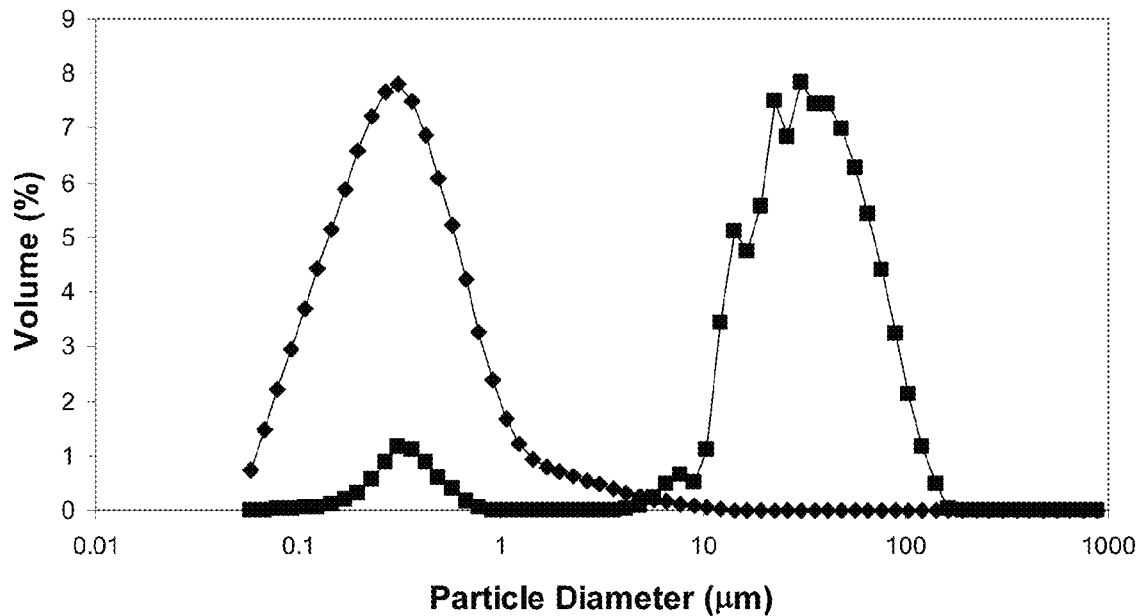
FIG. 4 is a plot of laser light scattering of particles formed by thin film freezing.

As shown in Table 3, the volume percentage of submicron particles, determined by laser light scattering, after sonication of the 5 mg/mL lysozyme formulation prepared by TFF at 223 K, ranged from 88 to 92%. The similarity in these two values was expected since the nearly identical thin film thicknesses would be expected to produce similar cooling rates. These values were similar to those for the SFL powders (36). For TFF, the protein powders were friable and could be broken up readily into submicron particles with minimal sonication. As shown in FIG. 4, the D(v,50) was 300 nm. In contrast, the same 5 mg/mL lysozyme formulation prepared by lyophilization had a very low fraction of 7% submicron particles shown in FIG. 4 and Table 3. As the lysozyme feed concentration was raised to 50 mg/mL the submicron fraction decreased to 66 and 62% on the 223 K and 133 K surfaces, respectively. The corresponding value for SFL was lower (48%), whereas for SFD it was higher (74%) (36). For the SFD powders, the D(v,50) was approximately 300 nm (36). A second peak with micron-sized particles was present for the 50 mg/mL lysozyme solution prepared by SFL and TFF as shown in Table 3. However, 50 mg/mL is an unusually high protein concentration and TFF would ordinarily be applied to concentrations on the order of 5 mg/mL, where the second larger peak is not present as shown in FIG. 4.

Figure 5A:
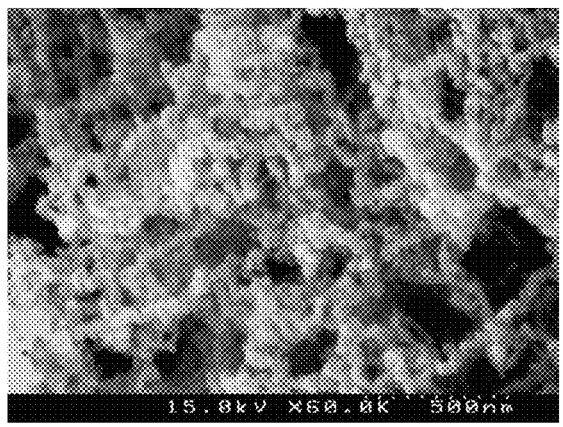
FIGS. 5A and 5B are scanning electron micrograph (SEM) images of particles from 5 mg/mL lysozyme solutions processed by thin film freezing at surface temperatures of 223 K, and 133K, respectively.
Figure 5B:
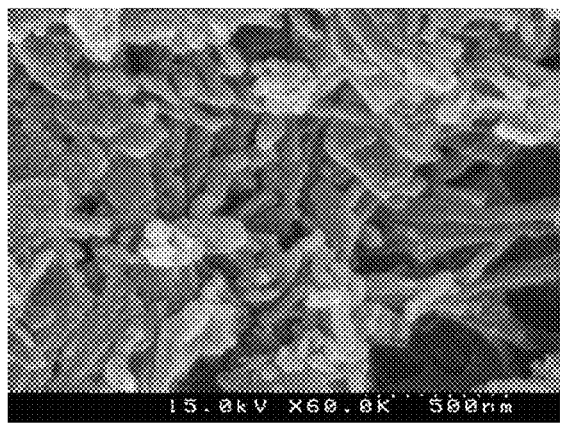
Figure 5C:
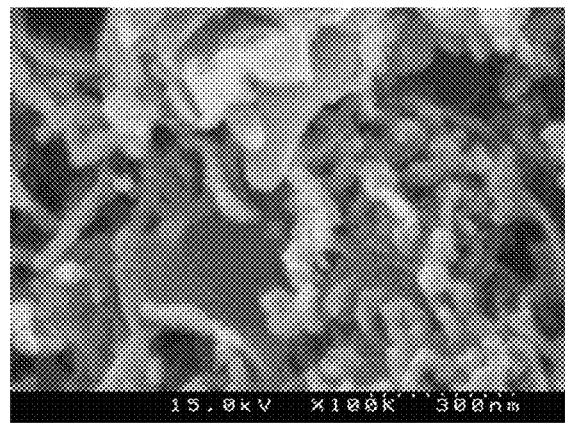
FIG. 5C is a scanning electron micrograph (SEM) of particles from 5 mg/mL lysozyme solutions using spray freezing into liquid with liquid nitrogen.
Figure 6A:
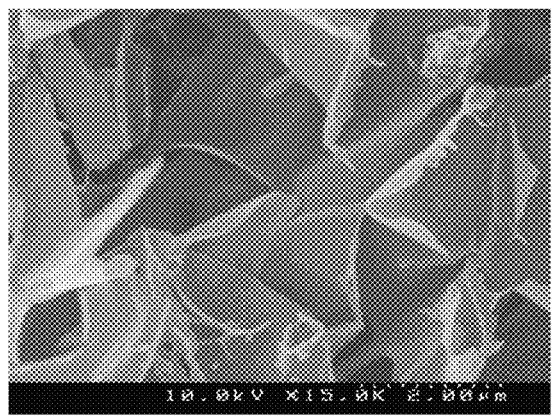
FIG. 6A to 6C are SEM images of particles from 50 mg/mL lysozyme solution processed by thin film freezing, by spray freezing into liquid nitrogen, and by spray freeze-drying-10 μm into liquid nitrogen, respectively.
Figure 6B:
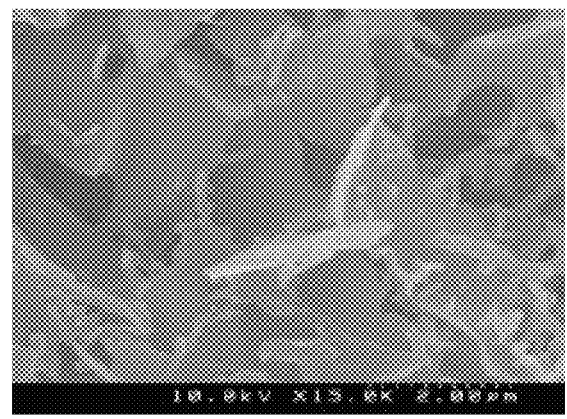
Figure 6C:
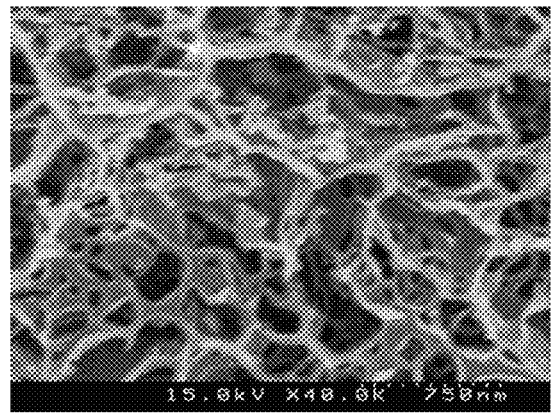

Selected SEM images from the results in Table 3 are shown in FIGS. 5 and 6. For 5 mg/mL lysozyme, fine 50 nm primary particles were produced by TFF at 223 K, demonstrated in FIG. 5A, comparable to those produced by SFL (36) in FIG. 5C. At 133 K, larger 50-100 nm diameter particles were mixed with rods 50-100 nm in diameter and more than 500 nm long as seen in FIG. 5B. The larger particles sizes shown in FIG. 5B compared to FIG. 5A are consistent with the slightly lower content of submicron particles measured by light scattering listed in Table 3.

For highly concentrated 50 mg/mL lysozyme solutions and a surface temperature of 223 K, large sheets were observed with features between 1 and 2 μm as shown in FIG. 6A. Similar features were observed for SFL (36). In contrast, a fine web with 100 nm features were produced by SFD (36) seen in FIG. 6C, which is consistent with the smaller particle sizes measured by light scattering in Table 3. The larger features observed in the TFF and SFL processes for 50 mg/mL versus 5 mg/mL solutions are consistent with the particle size distributions measured by light scattering. The similarity of the particle morphologies for the powders prepared by the SFL and TFF processes at both the 5 and 50 mg/mL concentrations are also examined in terms of cooling rates.

Modeling the cooling rate of thin films. Droplet spreading to form thin films of liquid metal and water droplets has been described in term of the Weber number, (inertial to interfacial forces) where is the impact velocity, is the droplet diameter, and is the droplet interfacial tension in air. For We>30 immediately before impacting the cooled solid substrate (42, 48-50, 56, 63) the droplets deformed into cylindrical thin films before freezing. For the low We<1 regime, impacting droplets froze as spherical domes with minimal droplet spreading (49, 64). For the falling liquid droplets, γ(air-water)=72 mN/m and $V=(2gH)^{1/2}$ (65) where the falling height, H, of the droplet was 10 cm, resulting in V=1.4 m/s. The observed formation of thin cylindrical disks was consistent with this We of 97, but when H was reduced to less than 1 cm (We=9.8) the impacting water droplets froze as spherical domes that were only 4 mm in diameter.

Previously, it was shown with IR imaging studies of thin films formed with acetonitrile and t-butanol that droplet spreading occurred within the first 10 ms interval indicating that the droplet spreading time was much less than the freezing time (45). The same behavior was observed in FIG. 2 for water. The prediction of the cooling rate of the film with a simplified analytical heat transfer model was in good agreement with laboratory produced IR data (45). Herein, this approach is extended to thin film freezing of water droplets.

Briefly, the model assumes that the droplet spreads to form a cylindrical film on a much shorter time scale than heat transfer. Since the height (thickness) of the thin film is on the order of 200-400 μm, relative to a much larger diameter of 10-12 mm, radial heat transfer is neglected. The thermal diffusivity, $\alpha=k/\rho^*C_p$, where k is the thermal conductivity, ρ is the density, and $C_p$ is the heat capacity, is treated as constant over the entire temperature range. For the case of freezing water the thermal diffusivities of water and ice are averaged. One-dimensional heat transfer for a finite slab with an insulating boundary condition on the top surface of the thin film (air) and a constant temperature boundary condition on the bottom is described by equation (2) (66):

$$T(x,t) = T_p + \frac{2}{L}\sum_{n=0}^{\infty} e^{-\alpha(2n+1)^2\pi^2 t/4L^2} \cos\frac{(2n+1)\pi x}{2L}$$
$$\left\{\frac{2L(-1)^{n+1}T_p}{(2n+1)\pi} + \int_0^L T_i \frac{\cos(2n+1)\pi x'}{2L} dx'\right\}$$

Equation (2)

where x is the distance from the top of the spread droplet, T is the temperature in the film, $T_p$ is the plate temperature in contact with the bottom thin film surface, and L is the film thickness.

Figure 7A:
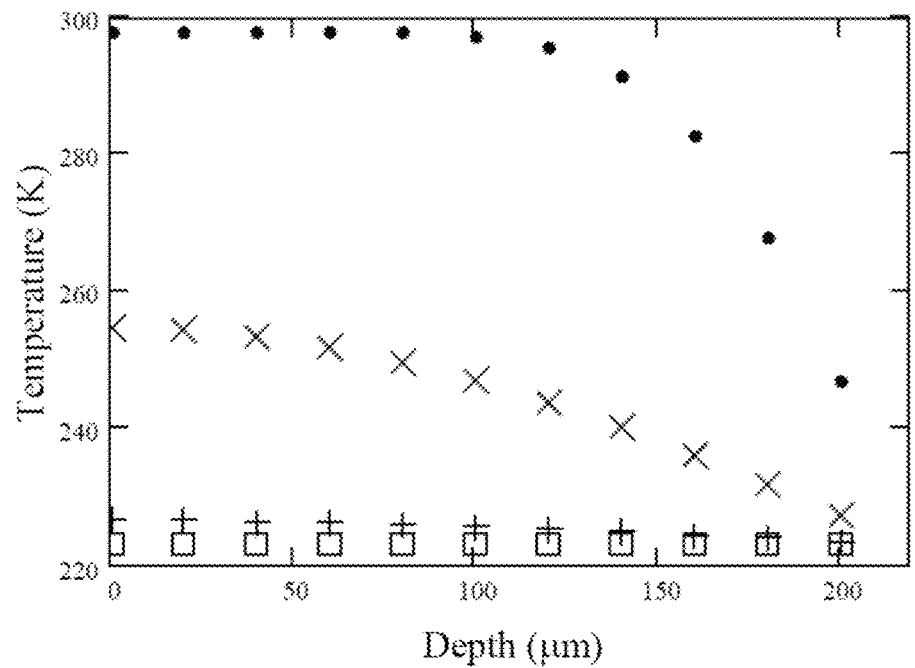
FIG. 7A is a graph of temperature versus depth profiles of thin aqueous films cooled on a surface at 223 K for a 220 μm thin film.
Figure 7B:
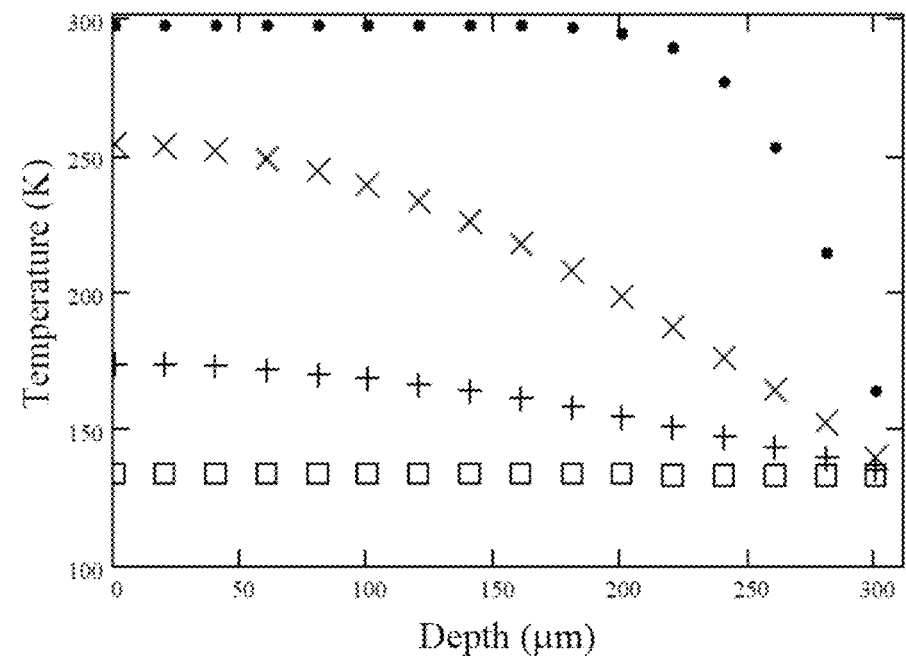
FIG. 7B is a graph of temperature versus depth profiles of thin aqueous films cooled on a surface at 133 K for a 320 μm thin film.

The calculated temperature profiles from equation (2) are shown in FIG. 7 and the calculated cooling rates and times are shown in Table 4 where calculated cooling rates, cooling times, and exposure time to the gas-liquid interface for SFD, SFL, and TFF are listed. The droplet dimensions are given in Table 1.

TABLE 4

|  | SFD[a] | SFL[a] | Thin Film from 3.6 mm Drop 223 K | Thin Film from 3.6 mm Drop 133 K |
| --- | --- | --- | --- | --- |
| Cooling Rate (K/s) | $3.8 \times 10^6$ | $7.2 \times 10^3$ | $3.9 \times 10^2$ | $2.0 \times 10^2$ |
| Cooling Time (ms) | 0.033 | 17 | $2.0 \times 10^2$ | $6.2 \times 10^2$ |
| Droplet Gas-Liquid Exposure Time (ms) | 10-1000 | 2 | ~1000 | ~1000 |

[a]Values taken from Engstrom et al. (36)

The cooling time was defined as the time for the temperature of the top surface of the film, T(0,t), to decrease from room temperature (25° C.) to a value 5% greater than that of the metal surface. The cooling rate (K/s) was then determined by dividing the temperature difference at the top of the film by the cooling time. As shown in FIG. 7A and Table 4, the predicted time to cool the top surface of the 220 μm thick thin film on the 223 K surface is $2.0 \times 10^2$ ms (cooling rate of $3.9 \times 10^2$ K/s). The calculated cooling rate is an order of magnitude less than for SFL ($7.2 \times 10^3$ K/s) and 4 orders of magnitude less than for SFD ($3.8 \times 10^6$ K/s). The much smaller cooling rates in TFF versus SFD may be explained by a 100 fold smaller surface area/volume ratio and a film thickness on the order of 20-30 times larger than the droplet radius in SFD.

The particle morphologies shown in FIG. 5 and particle SSAs in Table 3 were similar for freezing on the 223 K and 133 K surfaces, as a consequence of the rapid cooling in each case.

The testing cooling times to reach thermal equilibrium were longer by a factor of 3-4 compared to the modeled cooling times as demonstrated in Table 4. This difference is small compared to difference in orders of magnitude relative to other processes such as SFL and lyophilization. The difference may be the result of uncertainty in the calibration of the temperature measurement, differences in definitions of the final temperature for the model and IR camera, and the release of the heat of fusion of water which was not factored into the model. For extremely rapid cooling rates of water, the water may form a glass with limited crystallization (67). As shown by data and calculation, a cooling rate of $10^6$ K/s is necessary to vitrify water (67-70). The $10^2$ K/s cooling rate observed in TFF indicates that the latent heat of fusion may have been significant.

Nucleation and Growth Mechanisms versus Cooling Rate. To place the TFF results in perspective, it is instructive to consider the boundary conditions of extremely rapid vitrification/freezing in SFD and slow freezing in lyophilization. Previously, the morphologies of lysozyme powders prepared by SFL and SFD were shown to be similar for dilute 5 mg/mL lysozyme solutions. The SSAs were >100 m²/g for 50-100 nm spherical primary particles, despite a cooling rate of $10^3$ K/s for SFL versus $10^6$ K/s for SFD, as shown in Table 4 (36).

Figures 8A, 8B:
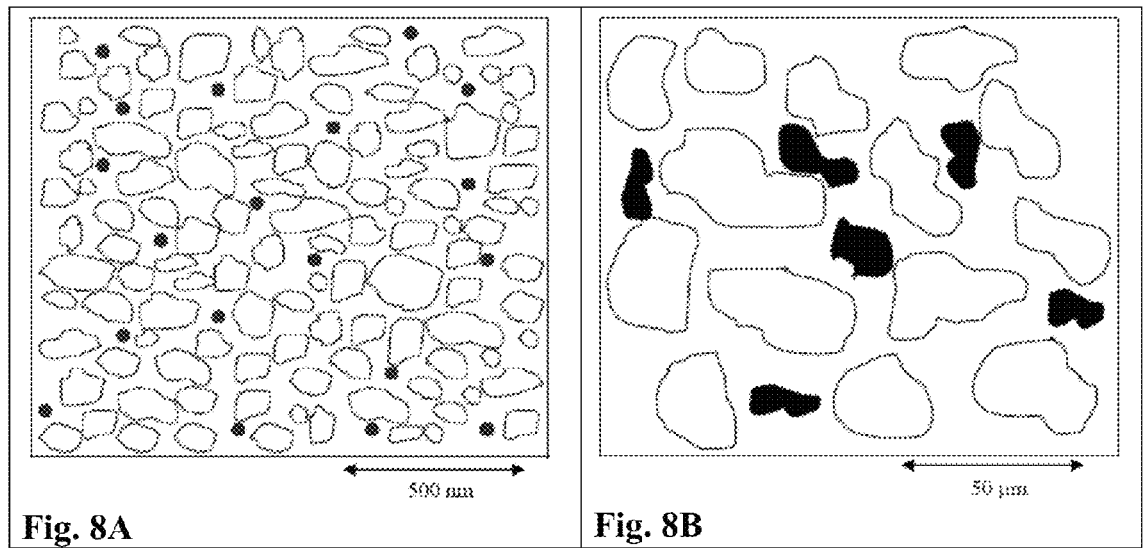
FIG. 8A is a picture of nucleation and growth of protein particle in unfrozen channels between glassy frozen water domains with high supercooling in the thin film freezing, spray freezing into liquid, and spray freeze-drying processes.
FIG. 8B is a picture of nucleation and growth of protein particle in unfrozen channels between glassy frozen water domains with low supercooling in shelf lyophilization.

The freezing mechanism involves many simultaneous changes in the properties of the unfrozen solution. As the water freezes, it changes concentrations, pH, ionic strength, viscosity, diffusion coefficients, collisions between nucleated particles and geometric size and shape of the unfrozen solution. The growth rate of the protein particles depends upon all of these factors, such that it would be challenging to develop a model for the final particle size. The thin liquid channels between the frozen water domains reduce the number of collisions between protein (sugar) particles and thus inhibit growth by coagulation, as shown in FIG. 8. Furthermore, the viscosity of the thin channels increases rapidly to arrest particle growth and the channel fully freezes. Furthermore, the sugar in the water raises the viscosity over that of pure water. For the case of slow cooling in lyophilization, the very low degree of supercooling creates relatively few nucleated ice domains compared to the rapid cooling processes, leaving thick channels of liquid solution between these domains. For a cooling rate of 1 K/min, as for the case of slowly cooling a 5 mg/mL solution in a −20° C. freezer, the lyophilized particle sizes were on the order of 30-100 µm. In these thick channels, the protein particles have sufficient time to aggregate and grow forming large particles before the channels are fully frozen. Although it is theoretically possible to mitigate this particle growth partially by reducing the protein solution concentration significantly below 1 mg/mL, such low protein concentrations can lead to excessive lyophilization requirements (21).

In SFD, the present inventors found that exposure of the protein to the gas-liquid interface has a larger effect on protein stability than to the ice-liquid or glassy water-liquid interface (19, 31, 32). It is unclear whether ice-liquid versus glassy water-liquid interfaces have different effects on protein stabilities (19, 20, 71). As described by previous references (68, 69), cooling rates on the order of $10^6$ K/s are needed to vitrify water, but the cooling rate necessary for vitrification can be lowered in the presence of sugar in solution (67, 70). For the slower cooling rates observed in TFF ($10^2$ K/s) relative to SFD, it is likely that ice particle domains instead of vitrified water domains are formed. The LDH activities were on the order of 100% for TFF. Thus, the present invention does not suggest that the ice-liquid interface has a detrimental effect on protein stability.

For the 5 mg/mL lysozyme formulation at 223 K, the SSA was quite large, although modestly smaller than for SFD, and the particle sizes after sonication were similar to those of both SFL and SFD as seen in Table 3. The lower cooling rate in TFF ($10^2$ K/s) compared to SFD ($10^6$ K/s) and SFL ($10^3$ K/s) was still sufficient to produce rapid nucleation and to prevent significant particle growth during freezing. However, for TFF, the size of the unfrozen channels was sufficiently thin and the increase in the viscosity of the unfrozen solution sufficiently fast to achieve similar particle sizes and morphologies as for the moderately faster process, SFL and much faster process, SFD. Thus, the extremely rapidly cooling rates in SFD were much faster than necessary to form submicron protein particles. A similar conclusion was reached in the comparison of SFL and SFD (32).

For 50 mg/mL highly concentrated solutions the larger volume fraction of vitrified solute domains in the unfrozen water channels lead to a greater collision frequency and increased particle growth (36). As observed previously (36), the slower cooling rate in SFL compared to SFD leads to greater particle growth before the large unfrozen liquid channels vitrify, leading to larger protein particles and lower powder SSAs (36). As shown in Table 3, the SSAs were similar for TFF and SFL. For these highly concentrated solutions, the larger particles formed in TFF (and SFL) versus SFD results from more time for growth in the thicker unfrozen channels. This limitation is typically not encountered in rapid freezing processes, as most previous studies examined much lower concentrations on the order of 5 mg/mL.

Figure 9:
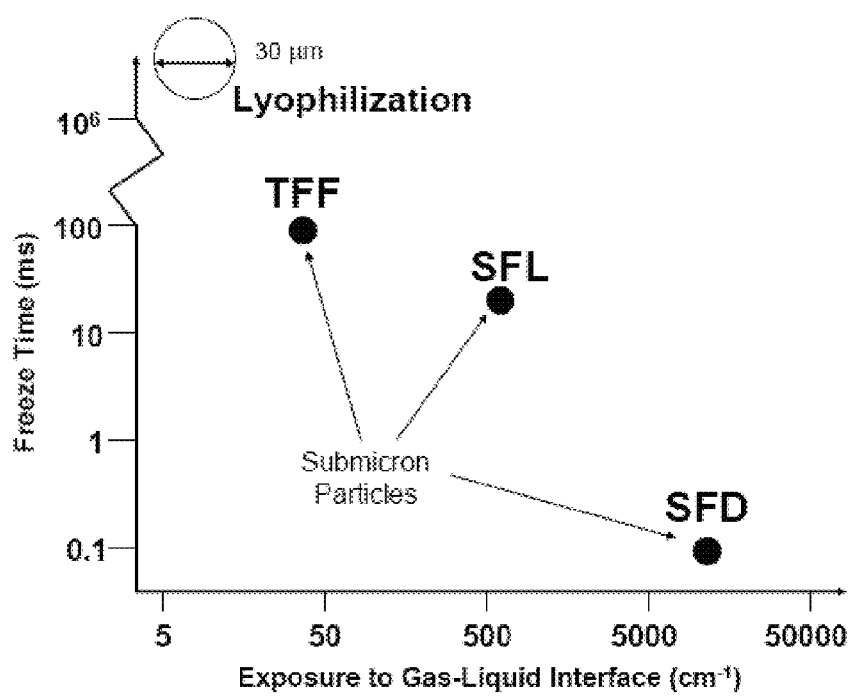
FIG. 9 is a graph of freezing time versus exposure to gas-liquid interface for lyophilization, thin film freezing (TFF), spray freezing into liquid (SFL), and spray freeze-drying (SFD).

Minimization of gas-liquid interface in TFF process. The LDH stabilities were essentially 100% after TFF indicating that none of the steps, droplet falling, spreading and freezing, and drying caused a measurable loss in enzyme activity. From previous calculations (32) it was shown that the exposure of the atomized droplets to the gas-liquid interface was an order of magnitude less in the SFL process (600 cm$^{-1}$) relative to SFD (6000 cm$^{-1}$) (19). This larger exposure to the gas-liquid interface resulted in lower LDH activities in SFD (32). In TFF the surface area/volume ratio of the gas-liquid interface of TFF (46 cm$^{-1}$) was 2 orders of magnitude lower than in SFD, leading to far less protein adsorption and aggregation. As shown in FIG. 9, the intermediate cooling rates in TFF and SFL offer a means to produce high surface area submicron particles as opposed to lyophilization, with smaller amounts of protein adsorption at gas-liquid interfaces compared to SFD resulting in higher protein stability.

Minimizing gas-liquid interface can improve protein stability by limiting the amount of protein that can adsorb to the interface. For surface active radiolabeled proteins, the surface excess concentration, Γ, (72, 73) at full saturation for β-casein, lysozyme, and BSA were 2.6, 3.0, and 3.3 mg/m², respectively (33, 72, 73). For LDH, we assumed a similar value of approximately 3 mg/m². For the top surface of a 12 mm diameter film, where the surface area is 1.13×10−4 m², the total adsorbed protein at equilibrium would be 3.4×10−4 mg. For a starting 3.6 mm liquid droplet containing 0.25 mg/mL LDH, the total protein is 6.2×10$^{-3}$ mg. Therefore, if all of the protein reached the interface and was denatured, the maximum decrease in protein activity would be 5.5%. The exposure of 1 s may not lead to full equilibrium adsorption. Furthermore, the increase in viscosity as a function of height and time with freezing will arrest diffusion of protein to the air-water interface. For ~10 µm diameter droplets in SFD, it was determined that 25-30% of the total LDH in the droplet adsorbs to the gas-liquid interface in only 0.4 ms (22). Denaturation of part of the adsorbed protein is consistent with the significant decreases in protein activity observed in the SFD process in Table 2.

The TFF process was utilized to produce 300 nm lysozyme particles with surface areas on the order of 31-73 m²/g and 100% LDH activities. Despite a cooling rate of ~$10^2$ K/s in TFF, the particle sizes and surface areas were similar to those observed in the widely reported process, spray freeze drying SFD, where cooling rates reach $10^6$ K/s. In TFF, the thin liquid channels between the ice domains were sufficiently thin and freezing rates of the thin channels sufficiently fast to achieve the similar particle morphologies. Therefore, the extremely rapid cooling rate in the SFD process was not necessary to form the desired submicron protein particles. Although LDH was exposed to the gas-liquid interface of the thin film for a maximum of ~1 s in TFF, the surface area/volume of 45 $cm^{-1}$ was sufficiently small that adsorption produced negligible aggregation and denaturation. Even if this gas-liquid interface became saturated with protein, followed by irreversible denaturation, the maximum activity loss for a 0.25 mg/mL LDH formulation would be 5%. For SFD with a droplet size of 10 µm, the maximum loss could reach 25% in just 0.4 ms from diffusion to the interface and adsorption (22), consistent with the significant decrease in enzyme activity (80%). In SFD, losses in protein stability have been observed in several previous studies (1, 11, 18, 19, 21). Although LDH stabilities are high in conventional lyophilization, cooling rates are on the order of 1 K/min resulting in large 30 to 100 µm sized particles (21). Thus, the intermediate cooling rate regime for TFF (and likewise for SFL), relative to SFD and lyophilization, offers a promising route to form stable submicron protein particles of interest in pulmonary and parenteral delivery applications.

Example 1. The solutions frozen using the TFF process has a final concentration of 5 mg Lysozyme/mL solvent where the solvent was a water/ethanol mixture at different concentration. The feed solution was then passed through a 17 gauge needle at a flow rate of 4 mL/min falling from a height of 10 cm onto a rotating stainless steel drum maintained at a temperature of 223 K where the droplets were allowed to spread into disks and freeze. The frozen disks were then lyophilized using the standard lyophilization procedure described above. The resulting particle sizes (FIG. 11) were measured using the Malvern Mastersizer as described previously.

Example 2: Solutions in varying initial concentrations of lysozyme in water were frozen as described above and then lyophilized to produce microparticles. The frozen particles were frozen on the rotating drum and then scrapped off into small vial for individual dosages. The particle sizes produced were measured using the Malvern Mastersizer as described above (FIG. 12).

FIGS. 13A to 13D compare the morphologies of TFF lysozyme prepared in glass vial versus TFF on a drum. Briefly, thin film freezing was performed directly in a vial that was cooled by submerging it partially in a liquid cryogenic fluid, or a fluid composed of dry ice and solvent. The feed was lysozyme at 5 mg/mL. The water in the frozen material was then removed by lyophilization of the vial. The product remained in the vial. A sample was removed from the vial and analyzed by scanning electron microscopy. The morphology was similar to a sample prepared directly on a metal drum. The advantage of this technique is that TFF may be performed directly in a glass vial to make particle with submicron features. The final dosage form may then be formulated by adding excipients to the particles in the vial.

TFF was performed using a feed of 150 mg/mL lysozyme in D.I. water. Once these samples were lyophilized, they were redispersed in acetonitrile to break the particles apart. The acetonitrile was then removed by TFF. The final particles after lyophilization were redispersed in benzyl benzoate to form a stable suspension (FIG. 14).

The present invention demonstrates a simple, efficient and robust process for freezing either small (<1 mL) quantities of protein solution or commercial quantities, that can produce stable submicron protein particles.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Y.-F. Maa and H. R. Costantino. Spray freeze-drying of biopharmaceuticals: applications and stability considerations. in: H. R. Costantino and M. J. Pikal (Eds), Biotechnology: Pharmaceutical Aspects. 2. Lyophilization of Biopharmaceuticals, Vol. 2 (H. R. Costantino and M. J. Pikal, eds), American Association of Pharmaceutical Scientists, Arlington, 2004, pp. 519-561.
2. Y.-F. Maa, L. Zhao, L. G. Payne, and D. Chen. Stabilization of alum-adjuvanted vaccine dry powder formulations: mechanism and application. Journal of Pharmaceutical Sciences 92:319-332 (2003).
3. X. M. Lam, E. T. Duenas, A. L. Daugherty, N. Levin, and J. L. Cleland. Sustained release of recombinant human insulin-like growth factor-I for treatment of diabetes. Journal of Controlled Release 67:281-292 (2000).
4. W. T. Leach, D. T. Simpson, T. N. Val, E. C. Anuta, Z. Yu, R. O. Williams III, and K. P. Johnston. Uniform encapsulation of stable protein nanoparticles produced by spray freezing for the reduction of burst release. Journal of Pharmaceutical Sciences 94:56-69 (2005).
5. O. L. Johnson, W. Jaworowicz, J. L. Cleland, L. Bailey, M. Charnis, E. Duenas, C. Wu, D. Shepard, S. Magil, T. Last, A. J. S. Jones, and S. D. Putney. The stabilization and encapsulation of human growth hormone into biodegradable microspheres. Pharmaceutical Research 14:730-735 (1997).
6. X. M. Lam, E. T. Duenas, and J. L. Cleland. Encapsulation and stabilization of nerve growth factor into poly(lactic-co-glycolic) acid microspheres. Journal of Pharmaceutical Sciences 90:1356-1365 (2001).
7. M. R. Prausnitz. Microneedles for transdermal drug delivery. Advanced Drug Delivery Reviews 56:581-587 (2004).
8. D. A. Edwards, J. Hanes, G. Caponetti, J. Hrkach, A. Ben-Jebria, M. L. Eskew, J. Mintzes, D. Deaver, N. Lotan, and R. Langer. Large porous particles for pulmonary drug delivery. Science 276:1868-1871 (1997).
9. S. J. Shire, Z. Shahrokh, and J. Liu. Challenges in the development of high protein concentration formulations. Journal of Pharmaceutical Sciences 93:1390-1402 (2004).
10. J. L. Cleland, E. T. Duenas, A. Park, A. Daugherty, J. Kahn, J. Kowalski, and A. Cuthbertson. Development of poly-(d,l-lactide-co-glycolide) microsphere formulations containing recombinant human vascular endothelial growth factor to promote local angiogenesis. Journal of Controlled Release 72:13-24 (2001).
11. X. C. Nguyen, J. D. Herberger, and P. A. Burke. Protein powders for encapsulation: a comparison of spray-freeze drying and spray drying of darbepoetin alfa. Pharmaceutical Research 21:507-514 (2004).
12. S. L. Lee, A. E. Hafeman, P. G. Debenedetti, B. A. Pethica, and D. J. Moore. Solid-State Stabilization of a-Chymotrypsin and Catalase with Carbohydrates. Industrial & Engineering Chemistry Research 45:5134-5147 (2006).
13. J. F. Carpenter, B. S. Chang, W. Garzon-Rodriguez, and T. W. Randolph. Rational design of stable lyophilized protein formulations: theory and practice. in: F. Carpenter John and C. Manning Mark (Eds), Pharmaceutical Biotechnology. 13. Rational Design of Stable Protein Formulations, Vol. 13 (F. Carpenter John and C. Manning Mark, eds), Kluwer Academic/Plenum Press, New York, 2002, pp. 109-133.
14. M. C. Manning, K. Patel, and R. T. Borchardt. Stability of protein pharmaceuticals. Pharmaceutical Research 6:903-918 (1989).
15. W. Wang. Lyophilization and development of solid protein pharmaceuticals. International Journal of Pharmaceutics 203:1-60 (2000).
16. R. A. DePaz, D. A. Dale, C. C. Barnett, J. F. Carpenter, A. L. Gaertner, and T. W. Randolph. Effects of drying methods and additives on the structure, function, and storage stability of subtilisin: role of protein conformation and molecular mobility. Enzyme and Microbial Technology 31:765-774 (2002).
17. M. J. Pikal. Mechanisms of protein stabilization during freeze-drying and storage: the relative importance of thermodynamic stabilization and glassy state relaxation dynamics. Drugs and the Pharmaceutical Sciences 137: 63-107 (2004).
18. H. R. Costantino, L. Firouzabadian, K. Hogeland, C. C. Wu, C. Beganski, K. G. Carrasquillo, M. Cordova, K. Griebenow, S. E. Zale, and M. A. Tracy. Protein spray-freeze drying. Effect of atomization conditions on particle size and stability. Pharmaceutical Research 17:1374-1383 (2000).
19. S. D. Webb, S. L. Golledge, J. L. Cleland, J. F. Carpenter, and T. W. Randolph. Surface adsorption of recombinant human interferon-g in lyophilized and spray-lyophilized formulations. Journal of Pharmaceutical Sciences 91:1474-1487 (2002).
20. B. S. Chang, B. S. Kendrick, and J. F. Carpenter. Surface-induced denaturation of proteins during freezing and its inhibition by surfactants. Journal of pharmaceutical sciences 85:1325-1330 (1996).
21. Y.-F. Maa and S. J. Prestrelski. Biopharmaceutical powders: particle formation and formulation considerations. Current Pharmaceutical Biotechnology 1:283-302 (2000).
22. M. Adler and G. Lee. Stability and surface activity of lactate dehydrogenase in spray-dried trehalose. Journal of Pharmaceutical Sciences 88:199-208 (1999).
23. J. Deng, D. R. Davies, G. Wisedchaisri, M. Wu, W. G. J. Hol, and C. Mehlin. An improved protocol for rapid freezing of protein samples for long-term storage. Acta Crystallographica, Section D: Biological Crystallography D60:203-204 (2004).
24. Y. Yamagata, T. Doen, N. Asakawa, and S. Takada, Process for producing protein powder 6723347, (2004).
25. Y.-F. Maa, P.-A. Nguyen, T. Sweeney, S. J. Shire, and C. C. Hsu. Protein inhalation powders: spray drying vs spray freeze drying. Pharmaceutical Research 16:249-254 (1999).
26. S. P. Sellers, G. S. Clark, R. E. Sievers, and J. F. Carpenter. Dry powders of stable protein formulations from aqueous solutions prepared using supercritical CO(2)-assisted aerosolization. Journal of pharmaceutical sciences 90:785-797 (2001).
27. J. D. Andya, Y.-F. Maa, H. R. Costantino, P.-A. Nguyen, N. Dasovich, T. D. Sweeney, C. C. Hsu, and S. J. Shire. The effect of formulation excipients on protein stability and aerosol performance of spray-dried powders of a recombinant humanized anti-IgE monoclonal antibody. Pharmaceutical Research 16:350-358 (1999).

28. Y.-F. Maa and P.-A. Nguyen, Method of spray freeze drying proteins for pharmaceutical administration, U.S. Pat. No. 6,284,282 (2001).
29. H. R. Costantino, L. Firouzabadian, C. C. Wu, K. G. Carrasquillo, K. Griebenow, S. E. Zale, and M. A. Tracy. Protein spray freeze drying. 2. Effect of formulation variables on particle size and stability. Journal of Pharmaceutical Sciences 91:388-395 (2002).
30. Z. H. Chang and J. G. Baust. Ultra-rapid freezing by spraying/plunging: pre-cooling in the cold gaseous layer. Journal of microscopy 161:435-444 (1991).
31. Z. Yu, K. P. Johnston, and R. O. Williams III. Spray freezing into liquid versus spray-freeze drying: Influence of atomization on protein aggregation and biological activity. European Journal of Pharmaceutical Sciences 27:9-18 (2006).
32. J. D. Engstrom, D. T. Simpson, C. Cloonan, E. Lai, R. O. Williams III, G. B. Kitto, and P. Johnston Keith. Stable high surface area lactate dehydrogenase particles produced by spray freezing into liquid nitrogen. European Journal of Pharmaceutics and Biopharmaceutics 65:163-174 (2007).
33. S. Magdassi and A. Kamyshny. Surface activity and functional properties of proteins. in: S. Magdassi (Ed), Surface Activity of Proteins (S. Magdassi, ed), Marcel Dekker, Inc., New York, 1996, pp. 1-38.
34. Z. Yu, A. S. Garcia, K. P. Johnston, and R. O. Williams III. Spray freezing into liquid nitrogen for highly stable protein nanostructured microparticles. European Journal of Pharmaceutics and Biopharmaceutics 58:529-537 (2004).
35. Z. Yu, T. L. Rogers, J. Hu, K. P. Johnston, and R. O. Williams III. Preparation and characterization of microparticles containing peptide produced by a novel process: spray freezing into liquid. European journal of pharmaceutics and biopharmaceutics 54:221-228 (2002).
36. J. D. Engstrom, D. T. Simpson, E. Lai, R. O. Williams III, and K. P. Johnston. Morphology of protein particles produced by spray freezing of concentrated solutions. European Journal of Pharmaceutics and Biopharmaceutics 65:149-162 (2007).
37. H. Sitte, L. Edelmann, and K. Neumann. Cryofixation without pretreatment at ambient pressure. in: R. A. Steinbrecht and K. Zierold (Eds), Cryotechniques in Biological Electron Microscopy (R. A. Steinbrecht and K. Zierold, eds), Springer-Verlag, Berlin, 1987, pp. 87-113.
38. J. C. Gilkey and L. A. Staehelin. Advances in ultrarapid freezing for the preservation of cellular ultrastructure. Journal of Electron Microscopy Technique 3:177-210 (1986).
39. J. A. N. Zasadzinski. A new heat transfer model to predict cooling rates for rapid freezing fixation. Journal of Microscopy 150:137-149 (1988).
40. J. E. Heuser, T. S. Reese, and D. M. Landis. Preservation of synaptic structure by rapid freezing. Cold Spring Harbor symposia on quantitative biology FIELD Publication Date: 1976 40:17-24. FIELD Reference Number: FIELD Journal Code: 1256107 FIELD Call Number: (1976).
41. J. Escaig. New instruments which facilitate rapid freezing at 83 K and 6 K. Journal of Microscopy (Oxford, United Kingdom) 126:221-230 (1982).
42. J. Fukai, T. Ozaki, H. Asami, and O. Miyatake. Numerical simulation of liquid droplet solidification on substrates. Journal of Chemical Engineering of Japan 33:630-637 (2000).
43. T. Bennett and D. Poulikakos. Splat-quench solidification: estimating the maximum spreading of a droplet impacting a solid surface. Journal of Materials Science 28:963-970 (1993).
44. H. Zhang, X. Y. Wang, L. L. Zheng, and X. Y. Jiang. Studies of splat morphology and rapid solidification during thermal spraying. International Journal of Heat and Mass Transfer 44:4579-4592 (2001).
45. K. A. Overhoff, J. D. Engstrom, B. Chen, T. L. Rogers, K. P. Johnston, and R. O. Williams III. Development and Optimization of the Novel Ultra-rapid Freezing Particle Engineering Process to Enhance the Dissolution Rates of Poorly Water Soluble Drugs. European Journal of Pharmaceutics and Biopharmaceutics 65:57-67 (2007).
46. J. Fukai, M. Tanaka, and O. Miyatake. Maximum spreading of liquid droplets colliding with flat surfaces. Journal of Chemical Engineering of Japan 31:456-461 (1998).
47. M. Pasandideh-Fard, R. Bhola, S. Chandra, and J. Mostaghimi. Deposition of tin droplets on a steel plate: simulations and experiments. International Journal of Heat and Mass Transfer 41:2929-2945 (1998).
48. M. Pasandideh-Fard, S. Chandra, and J. Mostaghimi. A three-dimensional model of droplet impact and solidification. International Journal of Heat and Mass Transfer 45:2229-2242 (2002).
49. D. Sivakumar and H. Nishiyama. Numerical analysis on the impact behavior of molten metal droplets using a modified splat-quench solidification model. Journal of Heat Transfer-Transactions of the Asme 126:1014-1022 (2004).
50. B. Kang, Z. Zhao, and D. Poulikakos. Solidification of liquid metal droplets impacting sequentially on a solid surface. Journal of Heat Transfer 116:436-45 (1994).
51. J. Madejski. Solidification of droplets on a cold surface. International Journal of Heat and Mass Transfer 19:1009-1013 (1976).
52. C. S. Marchi, H. Liu, E. J. Lavernia, R. H. Rangel, A. Sickinger, and E. Muehlberger. Numerical analysis of the deformation and solidification of a single droplet impinging onto a flat substrate. Journal of Materials Science 28:3313-21 (1993).
53. G. X. Wang and E. F. Matthys. Modeling of heat transfer and solidification during splat cooling: effect of splat thickness and splat/substrate thermal contact. International Journal of Rapid Solidification 6:141-74 (1991).
54. G. X. Wang and E. F. Matthys. Numerical modeling of phase change and heat transfer during rapid solidification processes: use of control volume integrals with element subdivision. International Journal of Heat and Mass Transfer 35:141-53 (1992).
55. Z. Zhao, D. Poulikakos, and J. Fukai. Heat transfer and fluid dynamics during the collision of a liquid droplet on a substrate. I. Modeling. International Journal of Heat and Mass Transfer 39:2771-2789 (1996).
56. Z. Zhao, D. Poulikakos, and J. Fukai. Heat transfer and fluid dynamics during the collision of a liquid droplet on a substrate. II. Experiments. International Journal of Heat and Mass Transfer 39:2791-2802 (1996).
57. G. Trapaga and J. Szekely. Mathematical modeling of the isothermal impingement of liquid droplets in spraying processes. Metallurgical Transactions B: Process Metallurgy 22B:901-14 (1991).
58. T. J. Anchordoquy and J. F. Carpenter. Polymers protect lactate dehydrogenase during freeze-drying by inhibiting dissociation in the frozen state. Archives of Biochemistry and Biophysics 332:231-238 (1996).

59. T. J. Anchordoquy, K.-I. Izutsu, T. W. Randolph, and J. F. Carpenter. Maintenance of quaternary structure in the frozen state stabilizes lactate dehydrogenase during freeze-drying. Archives of Biochemistry and Biophysics 390:35-41 (2001).
60. S. Brunauer, P. H. Emmett, and E. Teller. Adsorption of gases in multimolecular layers. Journal of the American Chemical Society 60:309-319 (1938).
61. E. H. Snell, R. A. Judge, M. Larson, and M. J. van der Woerd. Seeing the heat-preliminary studies of cryocrystallographyn using infrared imaging. Journal of Synchrotron Radiation 9:361-367 (2002).
62. A. A. Elkordy, R. T. Forbes, and B. W. Barry. Integrity of crystalline lysozyme exceeds that of a spray-dried form. International Journal of Pharmaceutics 247:79-90 (2002).
63. J. Fukai, Y. Shiiba, T. Yamamoto, O. Miyatake, D. Poulikakos, C. M. Megaridis, and Z. Zhao. Wetting Effects on the Spreading of a Liquid Droplet Colliding with a Flat Surface-Experiment and Modeling. Physics of Fluids 7:236-247 (1995).
64. S. Schiaffino and A. A. Sonin. Motion and arrest of a molten contact line on a cold surface: an experimental study. Physics of Fluids 9:2217-2226 (1997).
65. T. Bennett and D. Poulikakos. Heat-Transfer Aspects of Splat-Quench Solidification-Modeling and Experiment. Journal of Materials Science 29:2025-2039 (1994).
66. H. S. Carslaw and J. C. Jaeger. Conduction of Heat in Solids, Oxford University Press, London, 1959.
67. F. Franks Biophysics and Biochemistry at Low Temperatures, Cambridge University Press, New York, 1985.
68. P. G. Debenedetti. Supercooled and glassy water. Journal of Physics: Condensed Matter 15:R1669-R1726 (2003).
69. E. Mayer and P. Brueggeller. Vitrification of pure liquid water by high pressure jet freezing. Nature 298:715-718 (1982).
70. C. A. Angell. Liquid fragility and the glass transition in water and aqueous solutions. Chemical Reviews 102: 2627-2649 (2002).
71. C. A. Angell and L.-M. Wang. Hyperquenching and cold equilibration strategies for the study of liquid-liquid and protein folding transitions. Biophysical Chemistry 105: 621-637 (2003).
72. D. E. Graham and M. C. Phillips. Proteins at liquid interfaces. I. Kinetics of adsorption and surface denaturation. Journal of Colloid and Interface Science 70:403-14 (1979).
73. D. E. Graham and M. C. Phillips. Proteins at liquid interfaces. II. Adsorption Isotherms. Journal of Colloid and Interface Science 70:415-426 (1979).

What is claimed is:

1. A single-vial method for preparing micron-sized or submicron-sized particles comprising:
   reducing the temperature of a vial wherein the vial has a temperature differential of at least 30° C. between the solvent and the vial;
   spraying or dripping solvent droplets of a water soluble effective ingredient dissolved in one or more solvents directly into the vial such that the effective ingredient is exposed to a vapor-liquid interface of less than 500 $cm^{-1}$ area/volume, wherein the surface freezes the droplet into a thin film with a thickness of less than 500 micrometers and a surface area to volume between 25 to 500 $cm^{-1}$; and
   removing the solvent from the frozen material to form micron or submicron sized particles.

2. The method of claim 1, wherein the droplets freeze upon contact with the surface in about 50, 75, 100, 125, 150, 175, 200, 250, 500, 1,000 and 2,000 milliseconds.

3. The method of claim 1, wherein the droplets freeze upon contact with the surface in about 50 to 500 milliseconds.

4. The method of claim 1, wherein the droplets freeze upon contact with the surface in about 50 to 150 milliseconds.

5. The method of claim 1, wherein the droplet has a diameter between 0.1 and 5 mm at room temperature.

6. The method of claim 1, wherein the droplet has a diameter between 2 and 4 mm at room temperature.

7. The method of claim 1, wherein the droplet forms a thin film on the surface of between 50 and 500 micrometers in thickness.

8. The method of claim 1, wherein the droplets have a cooling rate of between 50-250 K/s.

9. The method of claim 1, wherein the vial is cooled by a cryogenic solid, a cryogenic gas, a cryogenic liquid, a freezing fluid, a freezing gas, a freezing solid, a heat exchanger, or a heat transfer fluid capable of reaching cryogenic temperatures or temperatures below the freezing point of the solvent.

10. The method of claim 1, wherein the vial, the water soluble effective ingredient and the one or more solvents are pre-sterilized prior to spraying or dripping.

11. The method of claim 1, wherein the step of spraying or dripping is repeated to overlay one or more thin films on top of each other to fill the vial to any desired level up to totally full.

12. The method of claim 1, further comprising the step of resuspending the composition in a solvent in an individually dosed vial to create a suspension or solution for delivery of the effective ingredient.

* * * * *